US009708371B2

(12) United States Patent
Kessler et al.

(10) Patent No.: US 9,708,371 B2
(45) Date of Patent: Jul. 18, 2017

(54) TREATMENTS FOR GASTROINTESTINAL DISORDERS

(75) Inventors: Marco Kessler, Danvers, MA (US); Angelika Fretzen, Somerville, MA (US); Hong Zhao, Lexington, MA (US); Robert Solinga, Brookline, MA (US); Vladimir Volchenok, Waltham, MA (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 364 days.

(21) Appl. No.: 14/239,178

(22) PCT Filed: Aug. 17, 2012

(86) PCT No.: PCT/US2012/051289
§ 371 (c)(1),
(2), (4) Date: Nov. 21, 2014

(87) PCT Pub. No.: WO2013/025969
PCT Pub. Date: Feb. 21, 2013

(65) Prior Publication Data
US 2015/0094272 A1    Apr. 2, 2015

Related U.S. Application Data

(60) Provisional application No. 61/524,699, filed on Aug. 17, 2011.

(51) Int. Cl.
| *C07K 7/08* | (2006.01) |
| *C11D 3/34* | (2006.01) |
| *C07K 7/54* | (2006.01) |
| *C07K 5/02* | (2006.01) |
| *A61K 38/10* | (2006.01) |
| *A61K 38/12* | (2006.01) |
| *A61K 45/06* | (2006.01) |

(52) U.S. Cl.
CPC ............ *C07K 7/08* (2013.01); *A61K 38/10* (2013.01); *A61K 38/12* (2013.01); *A61K 45/06* (2013.01); *C07K 5/02* (2013.01); *C07K 7/54* (2013.01); *C11D 3/3436* (2013.01); *G01N 2800/065* (2013.01)

(58) Field of Classification Search
None
See application file for complete search history.

(56) References Cited

U.S. PATENT DOCUMENTS

| 4,544,568 | A | 10/1985 | Heyland et al. |
| 4,806,524 | A | 2/1989 | Kawaguchi |
| 4,992,419 | A | 2/1991 | Woog et al. |
| 5,221,495 | A | 6/1993 | Cao |
| 5,451,410 | A | 9/1995 | Milstein |
| 5,593,696 | A | 1/1997 | McNally et al. |
| 5,654,278 | A | 8/1997 | Sorensen |
| 5,904,935 | A | 5/1999 | Eckenhoff et al. |
| 6,068,850 | A | 5/2000 | Stevenson et al. |
| 6,124,261 | A | 9/2000 | Stevenson et al. |
| 6,541,606 | B2 | 4/2003 | Margolin et al. |
| 6,734,162 | B2 | 5/2004 | Van Antwerp |
| 6,828,303 | B2 | 12/2004 | Kim et al. |
| 6,979,437 | B2 | 12/2005 | Bartus |
| 6,995,200 | B2 | 2/2006 | Krohnke |
| 7,056,942 | B2 | 6/2006 | Hildesheim et al. |
| 7,141,254 | B2 | 11/2006 | Bhaskaran et al. |
| 7,304,036 | B2 * | 12/2007 | Currie .................. C07K 14/245 514/12.2 |
| 7,351,798 | B2 | 4/2008 | Margolin et al. |
| 7,371,727 | B2 | 5/2008 | Currie et al. |
| 7,494,979 | B2 | 2/2009 | Currie et al. |
| 7,704,947 | B2 | 4/2010 | Currie et al. |
| 7,745,409 | B2 | 6/2010 | Currie et al. |

(Continued)

FOREIGN PATENT DOCUMENTS

| JP | 64-009938 | 1/1989 |
| JP | 2003-201256 | 7/2003 |

(Continued)

OTHER PUBLICATIONS

Maier et al. Analogues of Human Calcitonin II. Influence of Modifications in Amino Acid Positions 1, 8 and 22 on Hypocalcemic Activity in the Rat. Hormon. Metab. Res. 7 (1975) 511-514.*
Armed, Hashim and Shah, Navnit., "Formulations of Low Dose Medicines—Theory and Practice." American Pharmaceutical Review, 3(3): 1-4, 2000.
Andresen et al., "Effect of 5 days of linaclotide on transit and bowel function in females with constipation-predominant irritable bowel syndrome." Gastroenterology, 133(3):761-768, 2007.
Andresen et al., "Linaclotide Acetate." Drugs of the Future, 33(7): 570-576, 2008.
Angelastro et al., "An efficient synthesis of novel alpha-diketone and alpha-keto ester derivatives of N-protected amino acids and peptides." The Journal of Organic Chemistry, 54(16):3913-6, 1989.
Aventis Pharmaceuticals, Inc. (2002). DDAVP (desmopressin acetate) tablet, [Product Label]. Bridgewater, NJ 08807, USA.

(Continued)

*Primary Examiner* — Satyanarayana R Gudibande
*Assistant Examiner* — Jia-Hai Lee
(74) *Attorney, Agent, or Firm* — Honigman Miller Schwartz and Cohn LLP; Kelly T. Murphy; Jonathan P. O'Brien

(57) ABSTRACT

The present invention features peptides, compositions, and related methods for treating gastrointestinal disorders and conditions, including but not limited to, irritable bowel syndrome (IBS), gastrointestinal motility disorders, functional gastrointestinal disorders, gastroesophageal reflux disease (GERD), duodenogastric reflux, Crohn's disease, ulcerative colitis, inflammatory bowel disease, functional heartburn, dyspepsia, visceral pain, gastroparesis, chronic intestinal pseudo-obstruction (or colonic pseudo-obstruction), disorders and conditions associated with constipation, and other conditions and disorders are described herein, using peptides and other agents that activate the guanylate cyclase C (GC-C) receptor.

28 Claims, 3 Drawing Sheets

(56) References Cited

U.S. PATENT DOCUMENTS

| | | | |
|---|---|---|---|
| 7,767,644 B2 | 8/2010 | Schumann et al. | |
| 7,772,188 B2 | 8/2010 | Currie et al. | |
| 7,910,546 B2 | 3/2011 | Currie et al. | |
| 8,080,526 B2 * | 12/2011 | Currie | C07K 7/08 514/21.5 |
| 8,101,579 B2 | 1/2012 | Currie et al. | |
| 8,110,553 B2 | 2/2012 | Currie et al. | |
| 8,748,573 B2 * | 6/2014 | Fretzen | 530/327 |
| 8,802,628 B2 * | 8/2014 | Fretzen | A61K 9/1611 514/20.6 |
| 8,933,030 B2 | 1/2015 | Fretzen et al. | |
| 2003/0003563 A1 | 1/2003 | Vinkemeier et al. | |
| 2003/0069182 A1 | 4/2003 | Rinella | |
| 2003/0073628 A1 | 4/2003 | Shailubhai et al. | |
| 2003/0104996 A1 | 6/2003 | Li et al. | |
| 2003/0175230 A1 | 9/2003 | Dubief | |
| 2004/0265242 A1 | 12/2004 | Bartus | |
| 2004/0266989 A1 | 12/2004 | Currie | |
| 2005/0020811 A1 | 1/2005 | Currie et al. | |
| 2005/0080009 A1 | 4/2005 | Metzner et al. | |
| 2006/0258593 A1 | 11/2006 | Currie et al. | |
| 2007/0122354 A1 | 5/2007 | Hastedt et al. | |
| 2007/0154406 A1 | 7/2007 | Moon et al. | |
| 2007/0202165 A1 | 8/2007 | Heuer et al. | |
| 2007/0225216 A1 * | 9/2007 | Merzouk | A61K 38/12 514/13.3 |
| 2009/0110729 A1 | 4/2009 | Giovannone et al. | |
| 2009/0253634 A1 | 10/2009 | Currie et al. | |
| 2009/0305993 A1 | 12/2009 | Currie | |
| 2010/0048489 A1 | 2/2010 | Fretzen et al. | |
| 2010/0221329 A1 | 9/2010 | Shailubhai et al. | |
| 2012/0009225 A1 | 1/2012 | Fretzen et al. | |
| 2012/0039949 A1 | 2/2012 | Fretzen et al. | |
| 2012/0213846 A1 | 8/2012 | Fretzen et al. | |
| 2013/0012454 A1 | 1/2013 | Mo et al. | |
| 2013/0190239 A1 | 7/2013 | Fretzen et al. | |
| 2013/0273169 A1 | 10/2013 | Fretzen et al. | |

FOREIGN PATENT DOCUMENTS

| | | | |
|---|---|---|---|
| WO | WO9012029 | 10/1990 | |
| WO | WO9104743 | 4/1991 | |
| WO | WO9703692 | 2/1997 | |
| WO | WO9704796 | 2/1997 | |
| WO | WO9800152 | 1/1998 | |
| WO | WO9800157 | 1/1998 | |
| WO | WO0004880 | 2/2000 | |
| WO | WO0032172 | 6/2000 | |
| WO | WO0226248 | 4/2002 | |
| WO | WO02078683 | 10/2002 | |
| WO | WO03014304 | 2/2003 | |
| WO | WO03055511 | 7/2003 | |
| WO | WO02062369 | 8/2003 | |
| WO | WO2004052343 | 6/2004 | |
| WO | WO2004069165 | 8/2004 | |
| WO | WO2004108152 | 12/2004 | |
| WO | WO2005014025 | 2/2005 | |
| WO | WO2005042029 | 5/2005 | |
| WO | WO2005087797 | 9/2005 | |
| WO | WO2007022531 | 2/2007 | |
| WO | WO2007044375 | 4/2007 | |
| WO | WO2008006125 | 1/2008 | |
| WO | WO2008021133 | 2/2008 | |
| WO | WO2008027854 | 3/2008 | |
| WO | WO2008078189 | 7/2008 | |
| WO | WO2008106429 | 9/2008 | |
| WO | WO2008151257 | 12/2008 | |
| WO | 2010019266 A2 * | 2/2010 | A61K 38/10 |
| WO | WO2010019266 | 2/2010 | |
| WO | WO2010065524 | 6/2010 | |
| WO | WO2010065751 | 6/2010 | |
| WO | WO2011019819 | 2/2011 | |
| WO | WO2011056850 | 5/2011 | |

OTHER PUBLICATIONS

Bedu-Addo, F. et al., "Preformulation Development of Recombinant Pegylated Staphylokinase SY161 Using Statistical Design." AAPS PharmSci (http://www.aapspharmsci.org), 4(4) article 19, 1-11, 2002.

Bedu-Addo, F.K. et al., "Use of Biophysical Characterization in Preformulation Development of a Heavy-Chain Fragment of Botulinum Serotype B: Evaluation of Suitable Purification Process Conditions." Pharmaceutical Research, 21(8): 1353-1361, 2004.

Busby et al., "Linaclotide, through activation of guanylate cyclase C, acts locally in the gastrointestinal tract to elictly enhanced intestinal secretion and transit." Eur. J. Pharmacol., 649(1-3): 328-335, 2010.

Camilleri et al., "Challenges to the Therapeutic Pipeline for Irritable Bowel Syndrome: End Points and Regulatory Hurdles." Gastroenterology. 135:1877-1891, 2008.

Camilleri, "Management of the Irritable Bowel Syndrome" Gastroenterology, 120:652-668, 2001.

Capasso et al., "Deamidation via Cyclic Imide of Asparaginyl Peptides: Dependence on Salts, Buffers and Organic Solvents." Peptide Research, 4(4): 234-238, 1991.

Carpenter et al., "Rational Design of Stable Lyophilized Protein Formulations: Some Practical Advice." Pharmaceutical Research, 14(8): 969-975, 1997.

Carson et al.,"Effect of Linaclotide on Quality of Life in Adults With Chronic Constipation: Results From 2 Randomized, Double-Blind, Placebo-Controlled Phase III Trials." Gastroenterology, 139(1):E19, 2010.

Chourasia, M.K. and Jain, S.K., "Pharmaceutical approaches to colon targeted drug delivery systems." J Pharm Pharmaceut Sci (www.ualberta.ca/-csps), 6(1): 33-66, 2003.

Cleland et al., "The Development of Stable Protein Formulations: A Close Look at Protein Aggregation, Deamidation, and Oxidation." Critical Reviews in Therapeutic Drug Carrier Systems, 10(4): 307-377, 1993.

Constantino, H.R, et al., "Moisture-Induced Aggregation of Lyophilized Insulin". Pharmaceutical Research, 11(1): 21-29, 1994.

Cook et al., "Chronic constipation: Overview and Challenges." Neurogastroenterology and Motility, 21(supp2): 1-8, 2009.

Dulbecco et al., "Plaque formation and isolation of pure liner with poliomyelitis viruses." Journal of Experimental Medicine, 99(2): 167-182, 1954.

Elan Pharmaceuticals, Inc. (2004). PRIALT (ziconotide) injection, solution, [Product Label]. San Diego, CA 92121, USA.

Fix, J.A., "Oral Controlled Release Technology for Peptides: Status and Future Prospects." Pharmaceutical Research, 13(12): 1760-1764, 1996.

Forest, "Phase III randomized double-blind placebo-controlled trial of linaclotide administered to patients with chronic constipation." 2008. Retrieved from <<http:www.clinicaltrials.gov>> identifier NCT00765882 on Dec. 9, 2010.

Fu et al., "Protein Stability in Controlled-Release Systems." Nature Biotechnology, 18: 24-25, 2000.

Grenha et al., "Chitosan nanoparticles are compatible with respiratory epithelial cells in vitro." European Journal of Pharmaceutical Sciences, 31: 73-84, 2007.

Harris et al., "Drug evaluation: Linaclotide, a new direction in the treatment of irritable bowel syndrome and chronic constipation." Current Opinion in Molecular Therapeutics, 9(4):403-410, 2007.

Harris, "Constipation: Linaclotide—a stimulating new drug for chronic constipation." Nature Reviews Gastroenterology and Hepatology, 7(7):365-6, 2010.

"International Nonproprietary Names for Pharmaceutical Substances (INN)." WHO Drug Information, 21(3): 247-264, 2007.

Johnston et al., "Pilot study on the effect of linaclotide in patients with chronic constipation." Am. J. Gastroenterol., 104(1):125-132, 2009.

Kirby, "Oil-Based Formulations for Oral Delivery of Therapeutic Peptides." Journal of Liposome Research, 10(4): 391-407, 2000.

Langer, R. "Drug delivery and targeting", Nature; 392 (Supp): 5-10, 1998.

(56) References Cited

OTHER PUBLICATIONS

Lavins et al, "418 Effect of Linaclotide on Quality of Life in Adults with Chronic Constipation: Results from a Phase 2B Study." Gastroenterology, 136(5): A71, 2009.

Lechuga-Ballesteros et al., "Trileucine Improves Aerosol Performance and Stability of Spray-dried Powders for Inhalation." Journal of Pharmaceutical Sciences, 97(1): 287-302, 2008.

Lee et al., "Synthesis and biological activity of adipokinetic hormone analogues modified at the C-terminus." Peptides, 17(8): 1285-1290, 1996.

Lembo et al., "Linaclotide significantly improved bowel habits and relieved abdominal symptoms in adults with chronic constipation: Data from a large 4-week, randomized, double-blind, placebo-controlled study." Gastroenterology, 135 (1):295, 2008.

Lembo et al., "157 Effect of Linaclotide on IBS-C Symptoms in the First Week of Treatment: Results from a Phase 2B Study." Gastroenterology, 136(5):A30, 2009.

Maier et al., "Analogues of Human Calcitonin-II. Influence of Modifications in Amino Acid Positions 1, 8 and 22 on Hypocalcemic Activity in the Rat." Hormone and Metabolic Research, 7(06), 511-514, 1975.

Mehta, N.M., "Oral Delivery and Recombinant Production of Peptide Hormones. Part I: Making Oral Delivery Possible: Enteric-coated capsules or tablets with additional excipients enable intestinal delivery." Bio-Pharm International (www.biopharm-mag.com), 1-6, Jun. 2004.

Mehta, N.M., "Oral Delivery and Recombinant Production of Peptide Hormones. Part II: Recombinant Production of Therapeutic Peptides." Bio-Pharm International (www.biopharm-mag.com), 7-9, Jun. 2004.

Metz et al.: "Identification of Formaldehyde-induced Modifications in Proteins—Reactions with Model Peptides." Journal of Biological Chemistry, 279: 6235-6243, 2004.

Microbia, Forest, "Microbia and Forest Laboratories Announce Preliminary Results of Linaclotide Phase 2B Studies." Communications of Microbia, pp. 1-4, 2008.

Milic et al., "Semisynthesis of H-Ras with a glutamic acid methylester at position 61." Peptide Science, 90(3): 399-405, 2008.

Moss, "Peptide Notes", Retrived from <<www.alchemyst.co.uk/alchemystry/pdf/Organic/peptides.pdfl>>, 2003, 29 pages.

Oliyai et al., "Prodrugs of peptides and proteins for improved formulation and delivery." Annu. Rev. Pharmacol. Toxicol., 32:521-544, 1993.

Oliyai et al., "Chemical Pathways of Peptide Degradation. VII. Solid State Chemical Instability of an Aspartyl Residue in a Model Hexapeptide." Pharmaceutical Research, 11(6): 901-908, 1994.

Oliyai et al., "Solid State Chemical Instability of an Asparaginyl Residue in a Model Hexapeptide." Journal of Pharmaceutical Science & Technology, 48(3): 167-173, 1994.

Patel, K. and Borchardt, R.T., "Chemical Pathways of Peptide Degradation. III. Effect of Primary Sequence on the Pathways of Deamidation of Asparaginyl Residues in Hexapeptides." Pharmaceutical Research, 7(8): 787-793, 1990.

Patel, K. and Borchardt, R.T., "Deamidation of Asparaginyl Residues in Proteins: A Potential Pathway for Chemical Degradation of Proteins in Lyophilized Dosage Forms." Journal of Parenteral Science & Technology, 44(6): 300-301, 1990.

Patel et al., "Activated ketone based inhibitors of human renin." Journal of Medicinal Chemistry, 36(17):2431-47, 1993.

Rasmussen et al., "Prodrugs of peptides. 15. 4-Imidazolidinone prodrug derivatives of enkephalins to prevent aminopeptidase-catalyzed metabolism in plasma and absorptive mucosae." International Journal of Pharmaceutics, 76(1-2): 113-122, 1991.

Reporter'S Guide to Irritable Bowel Syndrome, retrieved from <<http:www.aboutibs.org/pdfs/ReportersGuideIBS.pdf>> on Nov. 28, 2012, total of 18 pages where the main text is numbered as pp. 1-14.

Sejourne, F. et al., "Development of a Novel Bioactive Formulation of Vasoactive Intestinal Peptide in Sterically Stabilized Liposomes." Pharmaceutical Research, 14(3): 362-365, 1997.

Shailubhai et al., "Uroguanylin treatment suppresses polyp formation in the Apc(Min/+) mouse and induces apoptosis in human colon adenocarcinoma cells via cyclic GMP." Cancer Res., 60:5151-5157, 2000.

Vippagunta et al., "Crystalline solids." Advanced Drug Delivery Reviews, 48:3-26, 2001.

\* cited by examiner

TREATMENTS FOR GASTROINTESTINAL DISORDERS

PRIORITY CLAIM

This application is a national phase application of PCT/US2012/051289, filed on Aug. 17, 2012, which claims priority to U.S. Provisional Application Ser. No. 61/524,699, filed Aug. 17, 2011. The entire contents of the aforementioned applications are incorporated herein by reference.

SEQUENCE LISTING

This application incorporates by reference in its entirety the Sequence Listing entitled "IW112PCT1US1a_ST25", containing 4.52 KB of data and last modified on May 11, 2016, in computer readable-format (CRF) and electronic .txt format, filed electronically herewith.

FIELD OF THE INVENTION

This invention relates to peptides, compositions and methods for treating gastrointestinal disorders.

BACKGROUND

Gastrointestinal disorders (GI) include irritable bowel syndrome (IBS) which is a common chronic disorder of the intestine that affects 20 to 60 million individuals in the US alone (Lehman Brothers, Global Healthcare-Irritable bowel syndrome industry update, September 1999). IBS is the most common disorder diagnosed by gastroenterologists and accounts for 12% of visits to primary care physicians (Camilleri 2001, Gastroenterology 120:652-668). In the US, the economic impact of IBS is estimated at $25 billion annually, through direct costs of health care use and indirect costs of absenteeism from work (Talley 1995, Gastroenterology 109:1736-1741). Patients with IBS have three times more absenteeism from work and report a reduced quality of life. There is a tremendous unmet medical need for patients suffering for IBS since few prescription options exist to treat IBS.

Patients with IBS suffer from abdominal pain and a disturbed bowel pattern. Three subgroups of IBS patients have been defined based on the predominant bowel habit: constipation-predominant irritable bowel syndrome (c-IBS), diarrhea-predominant irritable bowel syndrome (d-IBS) or alternating between the two irritable bowel syndromes (a-IBS). Estimates of individuals who suffer from c-IBS range from 20-50% of the IBS patients with 30% frequently cited. In contrast to the other two subgroups that have a similar gender ratio, c-IBS is more common in women (ratio of 3:1) (Talley et al. 1995, Am J Epidemiol 142:76-83).

The definition and diagnostic criteria for IBS have been formalized in the "Rome Criteria" (Drossman et al. 1999, Gut 45:Suppl II: 1-81), which are well accepted in clinical practice. Recently, there has been increasing evidence for a role of inflammation in etiology of IBS. Reports indicate that subsets of IBS patients have small but significant increases in colonic inflammatory and mast cells, increased inducible nitric oxide (NO) and synthase (iNOS) and altered expression of inflammatory cytokines (reviewed by Talley 2000, Medscape Coverage of DDW week).

Gastrointestinal disorders can also include constipation wherein as many as 34 million Americans suffer from symptoms associated with chronic constipation (CC) and 8.5 million patients have sought treatment. Patients with CC often experience hard and lumpy stools, straining during defecation, a sensation of incomplete evacuation, and fewer than three bowel movements per week. The discomfort and bloating of CC significantly affects patients' quality of life by impairing their ability to work and participate in typical daily activities.

Half of CC patients are not satisfied with currently available treatments for CC. Thus, there remains a need for new compounds and methods of treating CC.

U.S. Pat. Nos. 7,304,036 and 7,371,727 disclose peptides that act as agonists of the guanylate cyclase C (GC-C) receptor for the treatment of gastrointestinal disorders. One particular peptide disclosed is linaclotide, which consists of the following amino acid sequence: Cys Cys Glu Tyr Cys Cys Asn Pro Ala Cys Thr Gly Cys Tyr (SEQ ID NO: 1). These patents also disclose methods for preparing linaclotide and related peptides.

Linaclotide has the amino acid structure of:

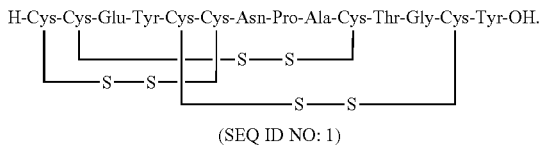

(SEQ ID NO: 1)

Linaclotide is orally administered and currently in clinical trials for treatment of irritable bowel syndrome with constipation (IBS-c) and chronic constipation (CC), has numerous effects on GI physiology including: (1) reduced visceral pain, (2) reduced bloating, and (3) increased GI transit, which can lead to increased stool frequency and improved stool consistency. Orally administered linaclotide acts locally by activating GC-C at the luminal surface; there are no detectable levels of linaclotide seen systemically after oral administration at therapeutic dose levels. Thus, the results from clinical trials of linaclotide, as well as preclinical studies that have been done with linaclotide and related peptides, suggest that GC-C peptide agonists may be used therapeutically.

The contents of the U.S. Pat. Nos. 7,304,036 and 7,371,727 are incorporated herein by reference in their entirety.

The present invention feature peptides which may be modified at their α-amine groups into ketone derivatives that are capable of activating and/or binding the guanylate cyclase-C (GC-C) receptors at different affinities. The present invention also features peptides that may be modified at their cysteine bonds with additional sulfur atoms and that may additionally be modified at their α-amine groups. GC-C is a key regulator in mammals of intestinal function, although low levels of GC-C have been detected in other tissues. GC-C responds to the endogenous hormones, guanylin and uroguanylin, and to enteric bacterial peptides from the heat stable enterotoxin family (ST peptide). When agonists bind to GC-C, there is an elevation of the second messenger, cyclic GMP (c-GMP), and an increase in chloride and bicarbonate secretion, resulting in an increase in intestinal fluid secretion. In some examples of the present invention, the peptides described herein may produce increased elevation of c-GMP levels and provide a therapeutic option for treating gastrointestinal disorders.

SUMMARY

The present invention features peptides, compositions, and related methods for treating gastrointestinal disorders and conditions, including but not limited to, irritable bowel syndrome (IBS) gastrointestinal motility disorders, constipation, functional gastrointestinal disorders, gastroesophageal reflux disease (GERD), duodenogastric reflux, Crohn's disease, ulcerative colitis, inflammatory bowel disease, functional heartburn, dyspepsia, visceral pain, gastroparesis, chronic intestinal pseudo-obstruction (or colonic pseudo-obstruction), and other conditions and disorders described herein using peptides and compositions that activate the guanylate cyclase C (GC-C) receptor.

One aspect of the present invention provides a peptide or a pharmaceutically acceptable salt thereof, wherein the peptide comprises the amino acid sequence Cys Cys Glu Tyr Cys Cys Asn Pro Ala Cys Thr Gly Cys Tyr (SEQ ID NO: 1), wherein the α-amine of the Cys$^1$ amino acid of the peptide is deaminated through oxidative or enzymatic reactions (the "Cys$^1$-α-ketone peptide").

In one embodiment, the peptide comprises the amino acid structure of:

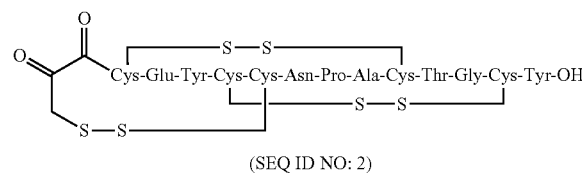

(SEQ ID NO: 2)

or a pharmaceutically acceptable salt thereof.

In another embodiment, the peptide comprises the amino acid structure of:

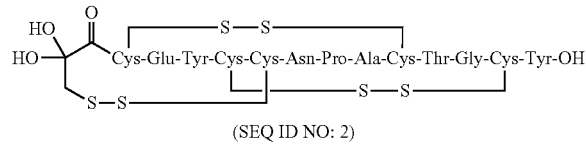

(SEQ ID NO: 2)

or a pharmaceutically acceptable salt thereof.

The details of one or more embodiments of the invention are set forth in the accompanying description.

Figure 1:
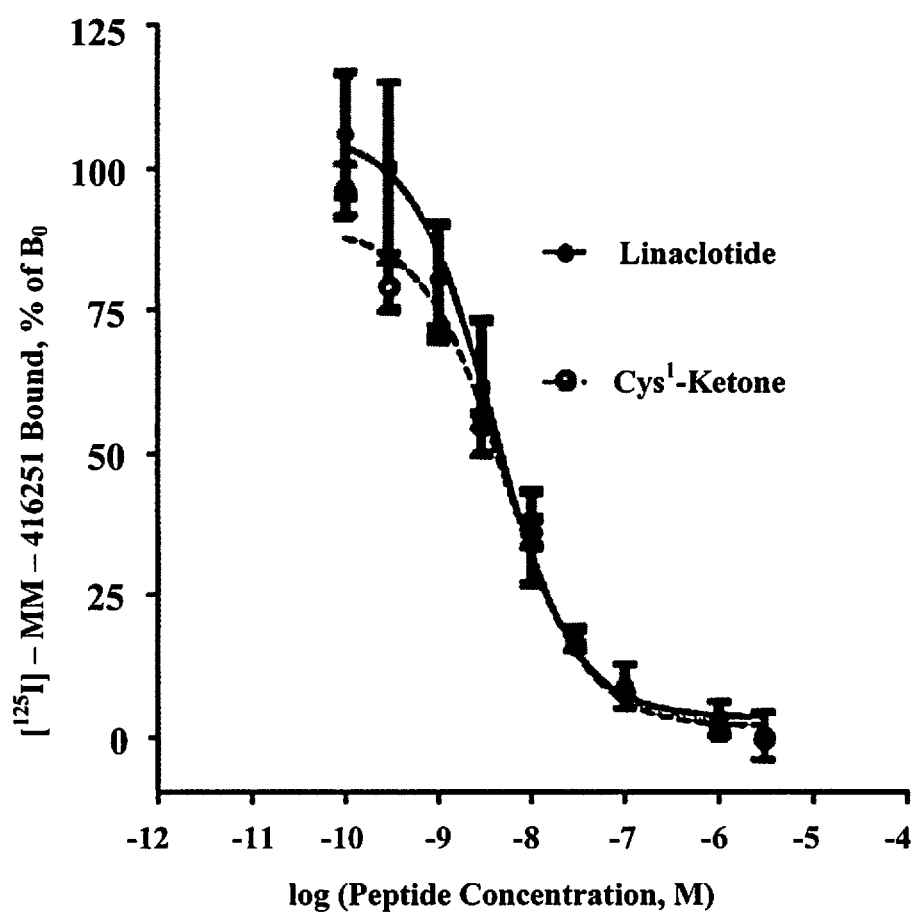
FIG. 1 shows specific binding of exemplary peptides of the present invention to cell-surface GC-C receptors on T84 cells in a competitive radioligand binding assay.

The figures are provided by way of example and are not intended to limit the scope of the present invention.

DETAILED DESCRIPTION

Guanylate cyclase C (GC-C) is a transmembrane receptor that is located on the apical surface of epithelial cells in the stomach and intestine. The receptor has an extracellular ligand-binding domain, a single transmembrane region and a C-terminal guanylyl cyclase domain. When a ligand binds to the extracellular domain of GC-C, the intracellular catalytic domain catalyzes the production of cGMP from GTP. In vivo, this increase in intracellular cGMP initiates a cascade of events that leads to increased secretion of chloride and bicarbonate into the intestinal lumen, increased luminal pH, decreased luminal sodium absorption, increased fluid secretion, and acceleration of intestinal transit. cGMP is secreted bidirectionally from the epithelium into the mucosa and lumen. The peptides and compositions of the present invention bind to the intestinal GC-C receptor which is a regulator of fluid and electrolyte balance in the intestine.

In some circumstances it can be desirable to treat patients with a variant or modified peptide that binds to and activates intestinal GC-C receptors, but is less active or more active than the non-variant form of a peptide. Reduced activity can arise from reduced affinity for the receptor or a reduced ability to activate the receptor once bound or reduced stability of the peptide. Increased activity can arise from increased affinity for the receptor or an increased ability to activate the receptor once bound or increased stability of the peptide.

Description of Exemplary Peptides:

In various embodiments, a peptide comprises the amino acid sequence Cys Cys Glu Tyr Cys Cys Asn Pro Ala Cys Thr Gly Cys Tyr (SEQ ID NO: 1), wherein the α-amine of the Cys$^1$ amino acid of the peptide is deaminated through oxidative reactions or enzymatic catalysis. This peptide may be produced, for example, by oxidative deamination of linaclotide involving nucleophilic attack of the α-amine of the Cys$^1$ amino acid which forms a Schiff base product, followed by prototropic tautomerization of the Schiff base, and finally hydrolysis in acid to give the α-Cys$^1$ ketone and its hydrate in equilibrium. This mixture of the two peptides will be referred as "Cys$^1$-α-Ketone" or "Cys$^1$-Ketone". These peptides may be tautomeric and the various tautomeric mixtures of different ratios can be useful and within the scope of the present invention.

In several embodiments, the peptide comprises the amino acid sequence Cys Cys Glu Tyr Cys Cys Asn Pro Ala Cys Thr Gly Cys Tyr (SEQ ID NO: 1), wherein the α-amine of the Cys$^1$ amino acid of the peptide is deaminated.

In one embodiment, the peptide comprises the amino acid structure of:

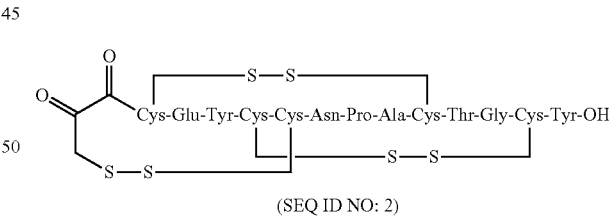

(SEQ ID NO: 2)

or a pharmaceutically acceptable salt thereof.

In another embodiment, the peptide comprises the amino acid structure of:

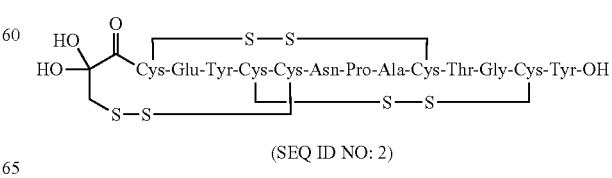

(SEQ ID NO: 2)

or a pharmaceutically acceptable salt thereof.

One skilled in the art would recognize that the peptide comprising the amino acid structure of:

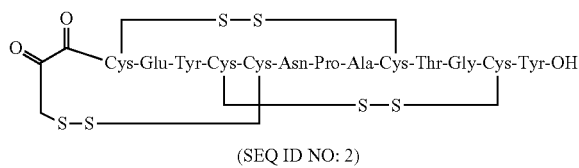

(SEQ ID NO: 2)

could be in equilibrium with its geminal diol monohydrate form comprising the amino acid structure of:

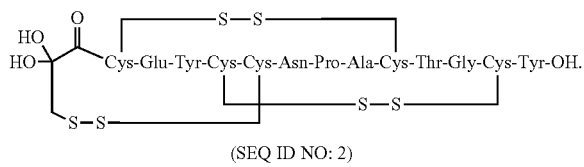

(SEQ ID NO: 2)

As used herein, the term "Cys1-α-ketone peptide" or the structure

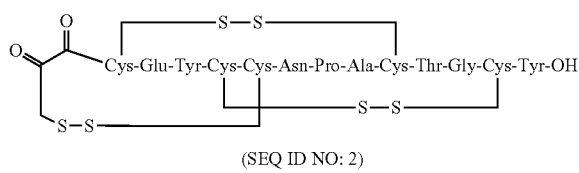

(SEQ ID NO: 2)

is intended to include both the Cys1-α-ketone structure and the germinal diol monohydrate form.

In another embodiment, a peptide comprises the amino acid sequence of Cys Cys Glu Tyr Cys Cys Asn Pro Ala Cys Thr Gly Cys Tyr (SEQ ID NO:1), wherein an additional sulfur atom may be attached to any one of the six cysteinyl sulfurs.

In one embodiment, the peptide comprises a linaclotide trisulfide product which forms with the addition of a single sulfur atom to one of the three disulfide cysteinyl bonds in linaclotide (referred herein as the "linaclotide trisulfide product" or "linaclotide trisulfide peptide").

In one embodiment, a peptide comprises the amino acid structure selected from:

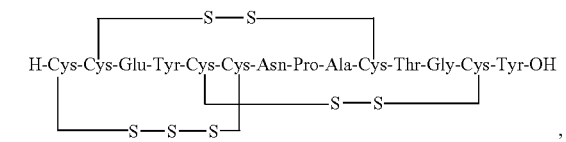

(SEQ ID NO: 3)

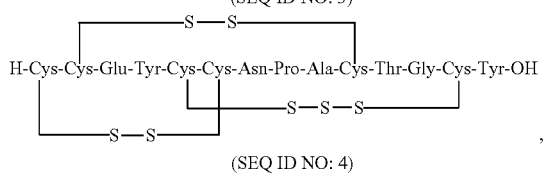

(SEQ ID NO: 4)

, and

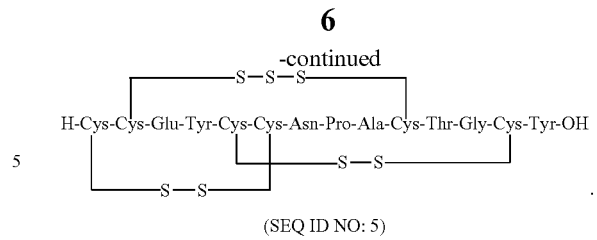

(SEQ ID NO: 5)

.

In a further embodiment, the peptide consists of the amino acid sequence Cys Cys Glu Tyr Cys Cys Asn Pro Ala Cys Thr Gly Cys Tyr (SEQ ID NO:1), wherein the α-amine of the Cys$^1$ amino acid of the peptide is deaminated.

In one embodiment, the peptide consists of the amino acid structure of:

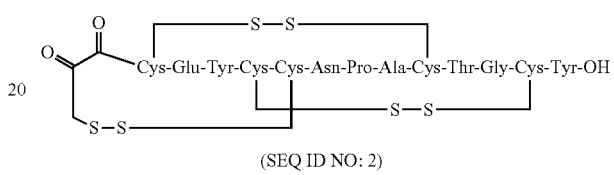

(SEQ ID NO: 2)

or a pharmaceutically acceptable salt thereof.

In one embodiment, the peptide consists of the amino acid structure of:

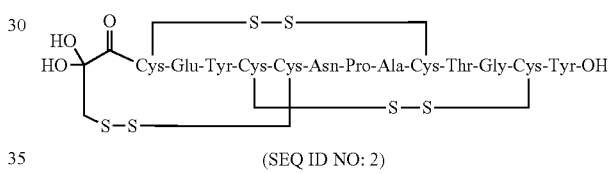

(SEQ ID NO: 2)

or a pharmaceutically acceptable salt thereof.

In another embodiment, the peptide consists of the amino acid sequence of Cys Cys Glu Tyr Cys Cys Asn Pro Ala Cys Thr Gly Cys Tyr (SEQ ID NO: 1) wherein an additional sulfur atom may be attached to any one of the six cysteinyl sulfurs.

In one embodiment, a peptide consists of the amino acid structure selected from:

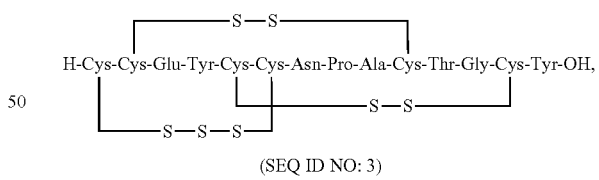

(SEQ ID NO: 3)

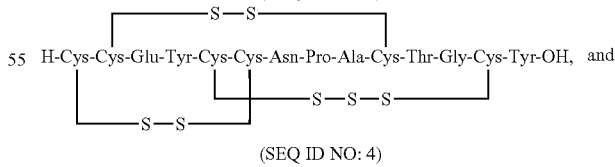

and (SEQ ID NO: 4)

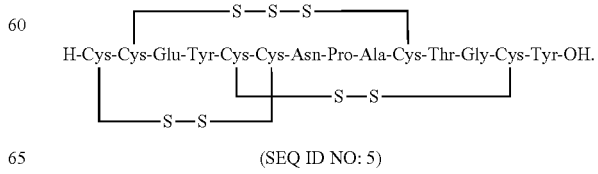

(SEQ ID NO: 5)

In some embodiments, the peptide or pharmaceutically acceptable salt thereof activates the guanylate cyclase C receptor.

In other embodiments, the peptide or pharmaceutically acceptable salt thereof comprises 30 or fewer amino acids.

In further embodiments, the peptide or pharmaceutically acceptable salt thereof comprises 20 or fewer amino acids.

In other embodiments, the peptide or pharmaceutically acceptable salt thereof comprises a peptide wherein fewer than five amino acids precede the first Cys residue of the amino acid sequence.

In some embodiments, the peptide or pharmaceutically acceptable salt thereof is isolated.

In other embodiments, the peptide or pharmaceutically acceptable salt thereof is purified.

In some embodiments, a pharmaceutically acceptable salt of the peptide is provided. In some instances, the pharmaceutically acceptable salt is a chloride salt.

Variant or Modified Peptides

In various embodiments, the peptide includes two Cys that form one disulfide bond, the peptide includes four Cys that form two disulfide bonds, or the peptide includes six Cys that form three disulfide bonds:

In various embodiments, the peptide includes two Cys that form one trisulfide bond, the peptide includes four Cys that form two trisulfide bonds, or the peptide includes six Cys that form three trisulfide bonds.

In some peptides one or both members of one or both pairs of Cys residues which normally form a disulfide bond can be replaced by homocysteine, penicillamine, 3-mercaptoproline (Kolodziej et al. 1996 *Int J Pept Protein Res* 48:274); β,β dimethylcysteine (Hunt et al. 1993 *Int J Pept Protein Res* 42:249) or diaminopropionic acid (Smith et al. 1978 *J Med Chem* 21:117) to form alternative internal cross-links at the positions of the normal disulfide bonds. In other embodiments, the disulfide bonds may be replaced by hydrocarbon crosslinking (Schafmeister et al. 2000 J Am Chem Soc 122:5891, Patgiri et al. 2008 Acc Chem Res 41:1289, Henchey et al. 2008 Curr Opin Chem Biol 12:692).

Production of Peptides

In one embodiment, peptides or precursor peptides of the invention can be produced recombinantly in any known protein expression system, including, without limitation, bacteria (e.g., *E. coli* or *Bacillus subtilis*), insect cell systems (e.g., *Drosophila* Sf9 cell systems), yeast cell systems (e.g., *S. cerevisiae*, *S. saccharomyces*) or filamentous fungal expression systems, or animal cell expression systems (e.g., mammalian cell expression systems). In some embodiments, recombinantly produced peptides may be chemically modified after they are expressed to form the peptides of the invention.

If the peptide or variant peptide is to be produced recombinantly, e.g., *E. coli*, the nucleic acid molecule encoding the peptide may also encode a leader sequence that permits the secretion of the mature peptide from the cell. Thus, the sequence encoding the peptide can include the pre sequence and the pro sequence of, for example, a naturally-occurring bacterial ST peptide. The secreted, mature peptide can be purified from the culture medium.

The sequence encoding a peptide described herein can be inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or M13 and derivatives thereof. Construction of a vector containing a nucleic acid described herein can be followed by transformation of a host cell such as a bacterium. Suitable bacterial hosts include but are not limited to, *E. coli, B. subtilis, Pseudomonas* and *Salmonella*. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during peptide production.

The protein coding sequence that includes a peptide described herein can also be fused to a nucleic acid encoding a peptide affinity tag, e.g., glutathione S-transferase (GST), maltose E binding protein, protein A, FLAG tag, hexahistidine, myc tag or the influenza HA tag, in order to facilitate purification. The affinity tag or reporter fusion joins the reading frame of the peptide of interest to the reading frame of the gene encoding the affinity tag such that a translational fusion is generated. Expression of the fusion gene results in translation of a single peptide that includes both the peptide of interest and the affinity tag. In some instances where affinity tags are utilized, DNA sequence encoding a protease recognition site will be fused between the reading frames for the affinity tag and the peptide of interest.

Genetic constructs and methods suitable for production of immature and mature forms of the peptides and variants described herein in protein expression systems other than bacteria, and well known to those skilled in the art, can also be used to produce peptides in a biological system.

In other embodiments, peptides containing amino acids not normally incorporated by the translation machinery and described above may be recombinantly produced by tRNA modification methods. Methods for modifying tRNA including, but not limited to, modifying the anti-codon, the amino acid attachment site, and/or the accepter stem to allow incorporation of unnatural and/or arbitrary amino acids are known in the art (Biochem. Biophys. Res. Comm. (2008) 372: 480-485; Chem. Biol. (2009) 16:323-36; Nat. Methods (2007) 4:239-44; Nat. Rev. Mol. Cell Biol. (2006) 7:775-82; Methods (2005) 36:227-238; Methods (2005) 36:270-278; Annu. Rev. Biochem. (2004) 73:147-176; Nuc. Acids Res. (2004) 32:6200-6211; Proc. Natl. Acad. Sci. USA (2003) 100:6353-6357; Royal Soc. Chem. (2004) 33:422-430).

In some embodiments, peptides may be chemically produced. Peptides can be synthesized by a number of different methods including solution and solid phase synthesis using traditional BOC or FMOC protection. For example, the peptide can be synthesized on 2-Chlorotrityl or Wang resin using consecutive amino acid couplings. The following protecting groups can be used: Fluorenylmethyloxycarbonyl or tert-butyloxycarbonyl (alpha-amino groups, N-terminus); trityl or tert-butyl (thiol groups of Cys); tert-butyl (γ-carboxyl of glutamic acid and the hydroxyl group of threonine, if present); and trityl (β-amid function of the asparagine side chain and the phenolic group of tyrosine, if present). Coupling can be effected with DIC and HOBt in the presence of a tertiary amine, and the peptide can be deprotected and cleaved from the solid support in using cocktail K (trifluoroacetic acid 81%, phenol 5%, thioanisole 5%, 1,2-ethanedithiol 2.5%, water 3%, dimethylsulphide 2%, ammonium iodide 1.5% w/w). After removal of trifluoroacetic acid and other volatiles the peptide can be precipitated using an organic solvent. Disulfide bonds between Cys residues can be formed using dimethyl sulfoxide (Tam et al. (1991) J. Am. Chem. Soc. 113:6657-62) or using an air oxidation strategy. The resulting peptide can be purified by reverse-phase chromatography and lyophilized. In some embodiments, chemically synthesized peptides may be chemically modified after they are synthesized to form the peptides of the invention.

These peptides can be made, isolated or used either in form of the base or as pharmaceutically acceptable salts thereof. Examples of salts include, without limitation, acetate, chloride, sulfate and phosphate salts of the peptide.

Compositions of Peptides and GC-C Receptor Agonists

In another aspect, pharmaceutical compositions are provided wherein the peptides, alone or in combination, can be combined with any pharmaceutically acceptable carrier or medium.

In several embodiments, the pharmaceutical composition comprises a peptide or pharmaceutically acceptable salt thereof as described herein. The pharmaceutical composition may comprise two or more peptides or pharmaceutically acceptable salts thereof described herein.

In some embodiments, the pharmaceutical composition comprises two or more peptides selected from:

i. a peptide or a pharmaceutically acceptable salt thereof, wherein the peptide comprises the amino acid structure of:

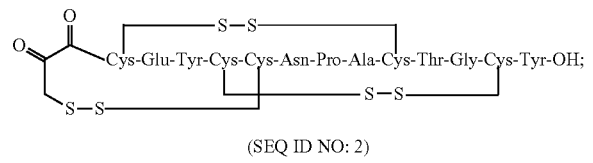

(SEQ ID NO: 2)

ii. a peptide or a pharmaceutically acceptable salt thereof, wherein the peptide comprises an amino acid structure of:

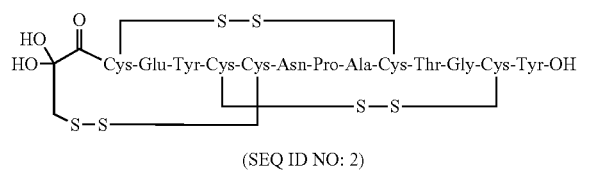

(SEQ ID NO: 2)

or iii. a peptide or a pharmaceutically acceptable salt thereof, wherein the peptide comprises the amino acid structure of:

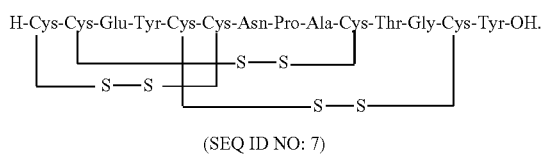

(SEQ ID NO: 7)

In other embodiments, the pharmaceutical composition comprises linaclotide and a peptide or a pharmaceutically acceptable salt thereof, wherein the peptide comprises an amino acid structure of:

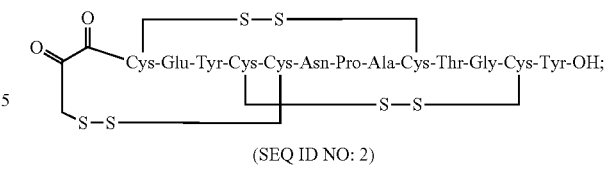

(SEQ ID NO: 2)

and the peptide or pharmaceutically acceptable salt thereof comprises less than 10%, 20%, 30%, 40%, 50%, 60%, 70%, 80%, or 90% by weight compared to the weight of linaclotide.

In further embodiments, the pharmaceutical composition comprises linaclotide and a peptide or a pharmaceutically acceptable salt thereof, wherein the peptide comprises an amino acid structure of:

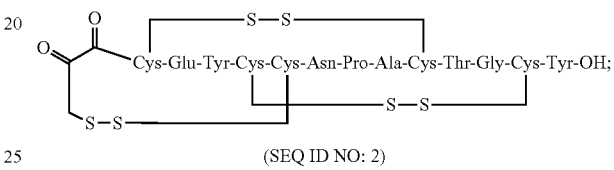

(SEQ ID NO: 2)

and wherein the pharmaceutical composition comprises less than 9%, 8%, 7%, 6%, 5%, 4%, 3%, 2%, 1% or 0.5% by weight of the peptide or pharmaceutically acceptable salt thereof as compared to the weight of linaclotide.

In further embodiments, the pharmaceutical composition comprises linaclotide and a peptide or a pharmaceutically acceptable salt thereof, wherein the peptide comprises an amino acid structure of:

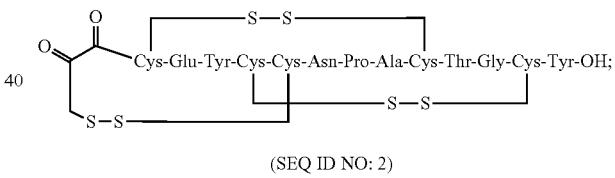

(SEQ ID NO: 2)

and wherein the pharmaceutical composition comprises about 0.01-9% by weight (e.g., about 0.01-8% by weight, about 0.01-7% by weight, about 0.01-6% by weight, about 0.01-5% by weight, about 0.01-4% by weight, about 0.01-3% by weight, about 0.01-2% by weight, about 0.01-2% by weight, about 0.01-1% by weight) of the peptide or pharmaceutically acceptable salt thereof as compared to the weight of linaclotide.

In other embodiments, the pharmaceutical composition comprises linaclotide and a peptide or a pharmaceutically acceptable salt thereof, wherein the peptide comprises an amino acid structure of:

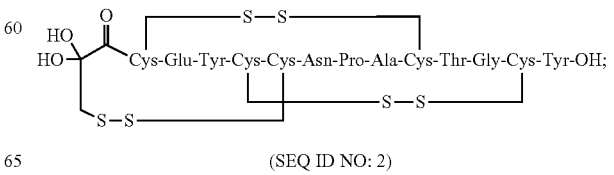

(SEQ ID NO: 2)

and the peptide or pharmaceutically acceptable salt thereof comprises less than 10%, 20%, 30%, 40%, 50%, 60%, 70%, 80%, or 90% by weight compared to the weight of linaclotide.

In further embodiments, the pharmaceutical composition comprises linaclotide and a peptide or a pharmaceutically acceptable salt thereof, wherein the peptide comprises an amino acid structure of:

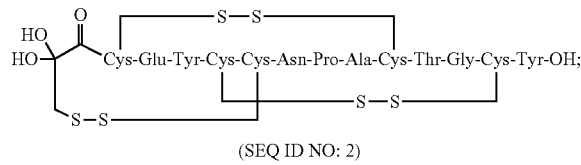

(SEQ ID NO: 2)

and the peptide or pharmaceutically acceptable salt thereof comprises less than 9%, 8%, 7%, 6%, 5%, 4%, 3%, 2%, 1% or 0.5% by weight compared to the weight of linaclotide.

In further embodiments, the pharmaceutical composition comprises linaclotide and a peptide or a pharmaceutically acceptable salt thereof, wherein the peptide comprises an amino acid structure of:

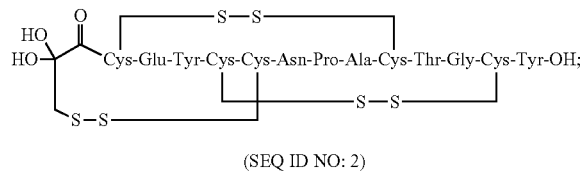

(SEQ ID NO: 2)

and wherein the pharmaceutical composition comprises about 0.01-9% by weight (e.g., about 0.01-8% by weight, about 0.01-7% by weight, about 0.01-6% by weight, about 0.01-5% by weight, about 0.01-4% by weight, about 0.01-3% by weight, about 0.01-2% by weight, about 0.01-2% by weight, about 0.01-1% by weight) of the peptide or pharmaceutically acceptable salt thereof as compared to the weight of linaclotide.

In other embodiments, the pharmaceutical composition comprises linaclotide and a peptide or a pharmaceutically acceptable salt thereof, wherein the peptide consists of the amino acid structure of:

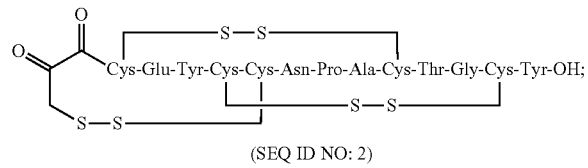

(SEQ ID NO: 2)

and the peptide or pharmaceutically acceptable salt thereof comprises less than 10%, 20%, 30%, 40%, 50%, 60%, 70%, 80%, or by weight compared to the weight of linaclotide.

In further embodiments, the pharmaceutical composition comprises linaclotide and a peptide or a pharmaceutically acceptable salt thereof, wherein the peptide consists of an amino acid structure of:

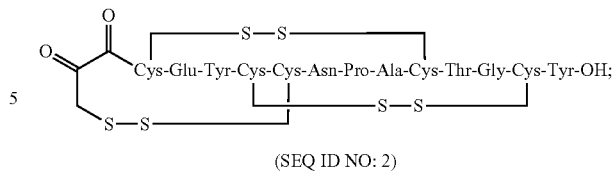

(SEQ ID NO: 2)

and the peptide or pharmaceutically acceptable salt thereof comprises less than 9%, 8%, 7%, 6%, 5%, 4%, 3%, 2%, 1%, or 0.5% by weight compared to the weight of linaclotide.

In further embodiments, the pharmaceutical composition comprises linaclotide and a peptide or a pharmaceutically acceptable salt thereof, wherein the peptide consists of an amino acid structure of:

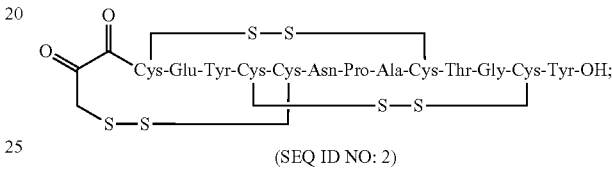

(SEQ ID NO: 2)

and wherein the pharmaceutical composition comprises about 0.01-9% by weight (e.g., about 0.01-8% by weight, about 0.01-7% by weight, about 0.01-6% by weight, about 0.01-5% by weight, about 0.01-4% by weight, about 0.01-3% by weight, about 0.01-2% by weight, about 0.01-2% by weight, about 0.01-1% by weight) of the peptide or pharmaceutically acceptable salt thereof as compared to the weight of linaclotide.

In other embodiments, the pharmaceutical composition comprises linaclotide and a peptide or a pharmaceutically acceptable salt thereof, wherein the peptide consists of an amino acid structure of:

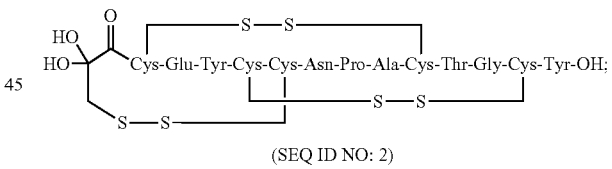

(SEQ ID NO: 2)

and the peptide or pharmaceutically acceptable salt thereof comprises less than 10%, 20%, 30%, 40%, 50%, 60%, 70%, 80%, or 90% by weight compared to the weight of linaclotide.

In further embodiments, the pharmaceutical composition comprises linaclotide and a peptide or a pharmaceutically acceptable salt thereof, wherein the peptide consists of an amino acid structure of:

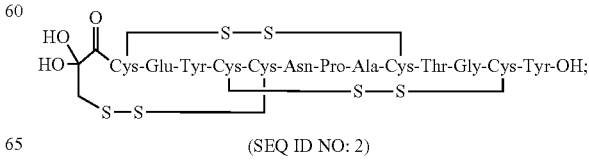

(SEQ ID NO: 2)

and the peptide or pharmaceutically acceptable salt thereof comprises less than 9%, 8%, 7%, 6%, 5%, 4%, 3%, 2%, 1%, or 0.5% by weight compared to the weight of linaclotide.

In further embodiments, the pharmaceutical composition comprises linaclotide and a peptide or a pharmaceutically acceptable salt thereof, wherein the peptide consists of an amino acid structure of:

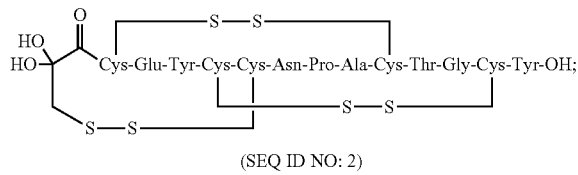

(SEQ ID NO: 2)

and wherein the pharmaceutical composition comprises about 0.01-9% by weight (e.g., about 0.01-8% by weight, about 0.01-7% by weight, about 0.01-6% by weight, about 0.01-5% by weight, about 0.01-4% by weight, about 0.01-3% by weight, about 0.01-2% by weight, about 0.01-2% by weight, about 0.01-1% by weight) of the peptide or pharmaceutically acceptable salt thereof as compared to the weight of linaclotide.

In some embodiments, the $Cys^1$-α-Ketone peptide comprises less than about 15% by weight of the composition, less than about 10% by weight of the composition, less than about 7% by weight of the composition, less than about 5% by weight of the composition, less than about 4% by weight of the composition, less than about 3% by weight of the composition, less than about 2% by weight of the composition, or less than about 1% by weight of the composition. In other exemplary embodiments, the $Cys^1$-α-Ketone peptide comprises from about 0.01% to about 15% by weight of the composition, about 0.05% to about 10% by weight of the composition, about 0.05% to about 7% by weight of the composition or about 0.05% to about 5% by weight of the composition. In further exemplary embodiments, the $Cys^1$-α-Ketone peptide comprises from about 0.5% to about 2% by weight of the composition.

In further embodiments, there is provided a method of treating a gastrointestinal disorder in a patient in need thereof comprising administering a pharmaceutical composition comprising of linaclotide and a $Cys^1$-α-Ketone peptide.

In some embodiments, there is provided a pharmaceutical composition comprising linaclotide and a linaclotide trisulfide product. In one embodiment, the linaclotide trisulfide product forms as the addition of a single sulfur atom to one of the three disulfide cysteinyl bonds in linaclotide. Three potential structure of the product is depicted below, although one of skill in the art will recognize that the sulfur atom may be attached to any one of the six cysteinyl sulfurs:

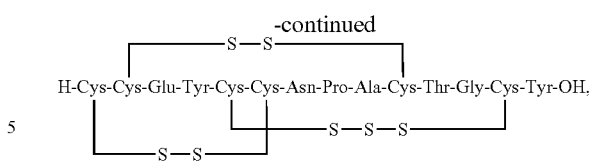

(SEQ ID NO: 3)

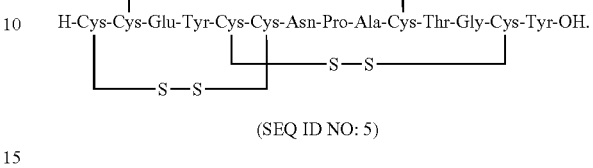

(SEQ ID NO: 4)

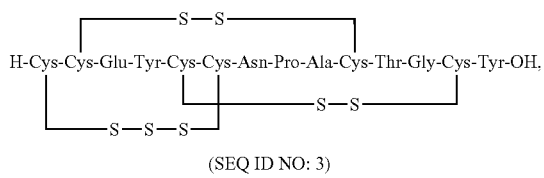

(SEQ ID NO: 5)

In another embodiment, there may be an addition of more than one sulfur atom to linaclotide, which would increase its molecular weight by 32 AU per added sulfur atom.

In some other embodiments, the linaclotide trisulfide product comprises less than about 15% by weight of the composition, less than about 10% by weight of the composition, less than about 7% by weight of the composition, less than about 5% by weight of the composition, less than about 4% by weight of the composition, less than about 3% by weight of the composition, less than about 2% by weight of the composition, or less than about 1% by weight of the composition.

In other exemplary embodiments, the linaclotide trisulfide product comprises from about 0.01% to about 15% by weight of the composition, about 0.05% to about 10% by weight of the composition, about 0.05% to about 7% by weight of the composition or about 0.05% to about 5% by weight of the composition. In further exemplary embodiments, the linaclotide trisulfide product comprises from about 0.5% to about 2% by weight of the composition.

In further embodiments, there is provided a method of treating a gastrointestinal disorder in a patient in need thereof comprising administering a pharmaceutical composition comprising of linaclotide and a linaclotide trisulfide product.

In other embodiments, the pharmaceutical composition consists essentially of a peptide or pharmaceutically acceptable salt thereof, wherein the peptide comprises the amino acid structure of:

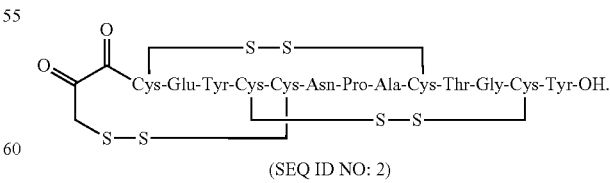

(SEQ ID NO: 2)

In other embodiments, the pharmaceutical composition consists essentially of a peptide or pharmaceutically acceptable salt thereof, wherein the peptide comprises the amino acid structure of:

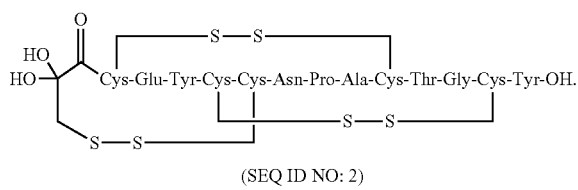

(SEQ ID NO: 2)

The term "consisting essentially of", and variants thereof, when used to refer to the composition, are used herein to mean that the composition includes a sole active peptide and other desired pharmaceutically inactive additives, excipients, and/or components (e.g., polymers, sterically hindered primary amines, cations, filling agents, binders, carriers, excipients, diluents, disintegrating additives, lubricants, solvents, dispersants, coating additives, absorption promoting additives, controlled release additives, anti-caking additives, anti-microbial additives, preservatives, sweetening additives, colorants, flavors, desiccants, plasticizers, dyes, or the like), and no other active pharmaceutical ingredient(s).

In some embodiments, there is provided a pharmaceutical composition comprising linaclotide, a $Cys^1$-α-Ketone peptide, and one or more peptides selected from:

i. a peptide ("$Cys^1$-IMD") or a pharmaceutically acceptable salt thereof, wherein the peptide comprises the amino acid structure of:

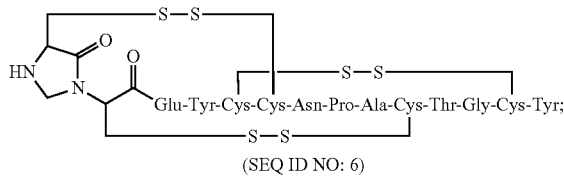

(SEQ ID NO: 6)

ii. a hydrolysis peptide ("$Asp^7$") or a pharmaceutically acceptable salt thereof, wherein the peptide comprises the amino acid structure of:

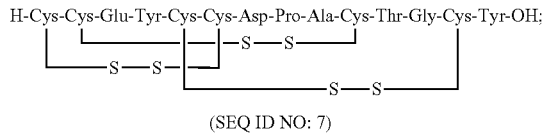

(SEQ ID NO: 7)

iii. an acetylation peptide ("$Cys^1$-N-Acetyl") or a pharmaceutically acceptable salt thereof, wherein the peptide comprises the amino acid structure of:

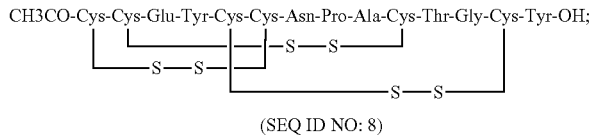

(SEQ ID NO: 8)

iv. a linaclotide trisulfide peptide or a pharmaceutically acceptable salt thereof, wherein the peptide comprises the amino acid sequence of Cys Cys Glu Tyr Cys Cys Asn Pro Ala Cys Thr Gly Cys Tyr (SEQ ID NO:1) wherein an additional sulfur atom may be attached to any one of the six cysteinyl sulfurs; and v. a peptide ("Des-$Tyr^{14}$") or a pharmaceutically acceptable salt thereof, wherein the peptide comprises the amino acid structure of:

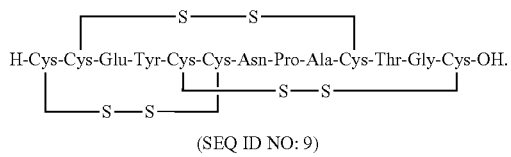

(SEQ ID NO: 9)

In some embodiments, the $Cys^1$-α-Ketone peptide comprises less than about 15% by weight of the composition, less than about 10% by weight of the composition, less than about 7% by weight of the composition, less than about 5% by weight of the composition, less than about 4% by weight of the composition, less than about 3% by weight of the composition, less than about 2% by weight of the composition, less than about 1.5% by weight of the composition, or less than about 1% by weight of the composition. In other exemplary embodiments, the $Cys^1$-α-Ketone peptide comprises from about 0.01% to about 15% by weight of the composition, about 0.05% to about 10% by weight of the composition, about 0.05% to about 7% by weight of the composition or about 0.05% to about 5% by weight of the composition.

In some embodiments, the $Cys^1$-IMD peptide comprises less than about 15% by weight of the composition, less than about 10% by weight of the composition, less than about 7% by weight of the composition, less than about 5% by weight of the composition, less than about 4% by weight of the composition, less than about 3.5% by weight of the composition, less than about 3% by weight of the composition, less than about 2% by weight of the composition, or less than about 1% by weight of the composition. In other exemplary embodiments, the $Cys^1$-IMD peptide comprises from about 0.01% to about 15% by weight of the composition, about 0.05% to about 10% by weight of the composition, about 0.05% to about 7% by weight of the composition or about 0.05% to about 5% by weight of the composition.

In some embodiments, the hydrolysis peptide ("$Asp^7$") comprises less than about 15% by weight of the composition, less than about 10% by weight of the composition, less than about 7% by weight of the composition, less than about 5% by weight of the composition, less than about 4% by weight of the composition, less than about 3.5% by weight of the composition, less than about 3% by weight of the composition, less than about 2% by weight of the composition, or less than about 1% by weight of the composition. In other exemplary embodiments, the hydrolysis peptide ("$Asp^7$") comprises from about 0.01% to about 15% by weight of the composition, about 0.05% to about 10% by weight of the composition, about 0.05% to about 7% by weight of the composition or about 0.05% to about 5% by weight of the composition.

In some embodiments, the acetylation peptide ("$Cys^1$-N-Acetyl") comprises less than about 15% by weight of the composition, less than about 10% by weight of the composition, less than about 7% by weight of the composition, less than about 5% by weight of the composition, less than about 4% by weight of the composition, less than about 3.5% by weight of the composition, less than about 3% by weight of the composition, less than about 2% by weight of the composition, or less than about 1% by weight of the composition. In other exemplary embodiments, the acetylation peptide ("$Cys^1$-N-Acetyl") comprises from about 0.01% to about 15% by weight of the composition, about 0.05% to about 10% by weight of the composition, about 0.05% to about 7% by weight of the composition or about 0.05% to about 5% by weight of the composition.

In some embodiments, the linaclotide trisulfide peptide comprises less than about 15% by weight of the composition, less than about 10% by weight of the composition, less than about 7% by weight of the composition, less than about 5% by weight of the composition, less than about 4% by weight of the composition, less than about 3.5% by weight of the composition, less than about 3% by weight of the composition, less than about 2% by weight of the composition, or less than about 1% by weight of the composition. In other exemplary embodiments, the linaclotide trisulfide peptide comprises from about 0.01% to about 15% by weight of the composition, about 0.05% to about 10% by weight of the composition, about 0.05% to about 7% by weight of the composition or about 0.05% to about 5% by weight of the composition.

In some embodiments, the Des-$Tyr^{14}$ peptide comprises less than about 15% by weight of the composition, less than about 10% by weight of the composition, less than about 7% by weight of the composition, less than about 5% by weight of the composition, less than about 4% by weight of the composition, less than about 3.5% by weight of the composition, less than about 3% by weight of the composition, less than about 2% by weight of the composition, or less than about 1% by weight of the composition. In other exemplary embodiments, the Des-$Tyr^{14}$ peptide comprises from about 0.01% to about 15% by weight of the composition, about 0.05% to about 10% by weight of the composition, about 0.05% to about 7% by weight of the composition or about 0.05% to about 5% by weight of the composition.

In some embodiments, the pharmaceutical composition comprises linaclotide, a $Cys^1$-α-Ketone peptide, and any desired concentration of disulfide bonded multimers.

In some embodiments, the composition comprises less than 10 wt. % of multimer(s).

In some embodiments, the composition comprises less than 7 wt. % of multimer(s).

In some embodiments, the composition comprises less than 6 wt. % of multimer(s).

In some embodiments, the composition comprises less than 5 wt. % of multimer(s).

In some embodiments, the composition comprises less than 4 wt % of multimer(s).

In some embodiments, the composition comprises less than 3 wt. % of multimer(s).

In some embodiments, the composition comprises less than 2 wt. % of multimer(s).

In some embodiments, the composition comprises less than 1 wt. % of multimer(s).

The peptides described herein can be combined with any pharmaceutically tolerable carrier or medium, e.g. solvents, dispersants, coatings, absorption promoting agents, controlled release agents, and one or more inert excipients (which include starches, polyols, granulating agents, microcrystalline cellulose (e.g. celphere, Celphere Beads®), diluents, lubricants, binders, disintegrating agents, and the like), etc. If desired, tablet dosages of the disclosed compositions may be coated by standard aqueous or nonaqueous techniques.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

As used herein, the term "binder" refers to any pharmaceutically acceptable binder that may be used in the practice of the invention. Examples of pharmaceutically acceptable binders include, without limitation, a starch (e.g., corn starch, potato starch and pre-gelatinized starch (e.g., STARCH 1500® and STARCH 1500 LM®, sold by Colorcon, Ltd.) and other starches), maltodextrin, gelatin, natural and synthetic gums such as acacia, powdered tragacanth, guar gum, cellulose or cellulose ether and its derivatives (e.g., methylcellulose, hydroxyethyl cellulose, hydroxyethyl methylcellulose, hydroxypropyl cellulose and hydroxypropyl methylcellulose (hypromellose), ethyl cellulose, cellulose acetate, carboxymethyl cellulose calcium, sodium carboxymethyl cellulose, carboxymethylcellulose, microcrystalline cellulose (e.g. AVICEL™, such as, AVICEL-PH-101™, -103™ and -105™, sold by FMC Corporation, Marcus Hook, Pa., USA)), polyvinyl alcohol, polyvinyl pyrrolidone (e.g., polyvinyl pyrrolidone K30, povidone), cellulose ether and mixtures thereof.

As used herein, the term "filler" refers to any pharmaceutically acceptable filler that may be used in the practice of the invention. Examples of pharmaceutically acceptable fillers include, without limitation, talc, calcium carbonate (e.g., granules or powder), dibasic calcium phosphate, tribasic calcium phosphate, calcium sulfate (e.g., granules or powder), microcrystalline cellulose (e.g., Avicel PH101 or Celphere CP-305), powdered cellulose, dextrates, kaolin, mannitol, silicic acid, sorbitol, starch (e.g., Starch 1500), pre-gelatinized starch, lactose, glucose, fructose, galactose, trehalose, sucrose, maltose, isomalt, raffinose, maltitol, melezitose, stachyose, lactitol, palatinite, xylitol, myoinositol, and mixtures thereof.

Examples of pharmaceutically acceptable fillers that may be particularly used for coating the peptides include, without limitation, talc, microcrystalline cellulose (e.g., Avicel PH101 or Celphere CP-305), micofine cellulose, powdered cellulose, dextrates, kaolin, mannitol, silicic acid, sorbitol, starch, pre-gelatinized starch, lactose, glucose, fructose, galactose, trehalose, sucrose, maltose, isomalt, dibasic calcium phosphate, raffinose, maltitol, melezitose, stachyose, lactitol, palatinite, xylitol, mannitol, myoinositol, and mixtures thereof.

As used herein, the term "additives" refers to any pharmaceutically acceptable additive. Pharmaceutically acceptable additives include, without limitation, disintegrants, dispersing additives, lubricants, glidants, antioxidants, coating additives, diluents, surfactants, flavoring additives, humectants, absorption promoting additives, controlled release additives, anti-caking additives, anti-microbial agents (e.g., preservatives), colorants, desiccants, plasticizers and dyes. As used herein, an "excipient" is any pharmaceutically acceptable additive, filler, binder or agent.

Compositions of the present invention may also optionally include other therapeutic ingredients, anti-caking agents, preservatives, sweetening agents, colorants, flavors, desiccants, plasticizers, dyes, glidants, anti-adherents, antistatic agents, surfactants (wetting agents), antioxidants, film-coating agents, and the like. Any such optional ingredient must be compatible with the compound described herein to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

The compositions can include, for example, various additional solvents, dispersants, coatings, absorption promoting additives, controlled release additives, and one or more inert additives (which include, for example, starches, polyols, granulating additives, microcrystalline cellulose, diluents, lubricants, binders, disintegrating additives, and the like), etc. If desired, tablet dosages of the disclosed compositions may be coated by standard aqueous or nonaqueous techniques. Compositions can also include, for example, anti-caking additives, preservatives, sweetening additives, colorants, flavors, desiccants, plasticizers, dyes, and the like.

Suitable disintegrants include, for example, agar-agar, calcium carbonate, microcrystalline cellulose, croscarmellose sodium, crospovidone, povidone, polacrilin potassium, sodium starch glycolate, potato or tapioca starch, other starches, pre-gelatinized starch, clays, other algins, other celluloses, gums, and mixtures thereof.

Suitable lubricants include, for example, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Evonik Degussa Co., Plano, Tex. USA), a pyrogenic silicon dioxide (CAB-O-SIL, Cabot Co., Boston, Mass. USA), and mixtures thereof.

Suitable glidants include, for example, leucine, colloidal silicon dioxide, magnesium trisilicate, powdered cellulose, starch, talc, and tribasic calcium phosphate.

Suitable anti-caking additives include, for example, calcium silicate, magnesium silicate, silicon dioxide, colloidal silicon dioxide, talc, and mixtures thereof.

Suitable anti-microbial additives that may be used, e.g., as a preservative for the peptides compositions, include, for example, benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, and mixtures thereof.

Suitable antioxidants include, for example, BHA (butylated hydroxyanisole), BHT (butylated hydroxytoluene), vitamin E, propyl gallate, ascorbic acid and salts or esters thereof, tocopherol and esters thereof, alpha-lipoic acid and beta-carotene.

Suitable coating additives include, for example, sodium carboxymethyl cellulose, cellulose acetate phthalate, ethylcellulose, gelatin, pharmaceutical glaze, hydroxypropyl cellulose, hydroxypropyl methylcellulose, hydroxypropyl methyl cellulose phthalate, methylcellulose, polyethylene glycol, polyvinyl acetate phthalate, shellac, sucrose, titanium dioxide, carnauba wax, microcrystalline wax, and mixtures thereof. Suitable protective coatings include Aquacoat (e.g. Aquacoat Ethylcellulose Aqueous Dispersion, 15% w/w, FMC Biopolymer, ECD-30), Eudragit (e.g. Eudragit E PO PE-EL, Roehm Pharma Polymers) and Opadry (e.g Opadry AMB dispersion, 20% w/w, Colorcon).

In certain embodiments, suitable additives for the peptides composition include one or more of sucrose, talc, magnesium stearate, crospovidone or BHA.

The compositions of the present invention can also include other excipients, agents, and categories thereof including but not limited to L-histidine, Pluronic®, Poloxamers (such as Lutrol® and Poloxamer 188), ascorbic acid, glutathione, permeability enhancers (e.g. lipids, sodium cholate, acylcarnitine, salicylates, mixed bile salts, fatty acid micelles, chelators, fatty acid, surfactants, medium chain glycerides), protease inhibitors (e.g. soybean trypsin inhibitor, organic acids), pH lowering agents and absorption enhancers effective to promote bioavailability (including but not limited to those described in U.S. Pat. No. 6,086,918 and U.S. Pat. No. 5,912,014), materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); soft gelatin capsules (like sorbitol special solution); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD& C Yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, manitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

In some embodiments, there is provided a pharmaceutical composition comprising a peptide described herein and one or more agents selected from $Mg^{2+}$, $Ca^{2+}$, $Zn^{2+}$, $Mn^{2+}$, $K^+$, $Na^+$ or $Al^{3+}$, a combination thereof, and/or a sterically hindered primary amine.

In further embodiments, the agent is $Mg^{2+}$, $Ca^{2+}$ or $Zn^{2+}$ or a combination thereof. In some embodiments, the cation is provided, without limitation, as magnesium acetate, magnesium chloride, magnesium phosphate, magnesium sulfate, calcium acetate, calcium chloride, calcium phosphate, calcium sulfate, zinc acetate, zinc chloride, zinc phosphate, zinc sulfate, manganese acetate, manganese chloride, manganese phosphate, manganese sulfate, potassium acetate, potassium chloride, potassium phosphate, potassium sulfate, sodium acetate, sodium chloride, sodium phosphate, sodium sulfate, aluminum acetate, aluminum chloride, aluminum phosphate or aluminum sulfate. In further embodiments, the cation is provided as magnesium chloride, calcium chloride, calcium phosphate, calcium sulfate, zinc acetate, manganese chloride, potassium chloride, sodium chloride or aluminum chloride. In other embodiments, the cation is provided as calcium chloride, magnesium chloride or zinc acetate.

In another embodiment, the agent is a sterically hindered primary amine.

In a further embodiment, the sterically hindered primary amine is an amino acid.

In yet a further embodiment, the amino acid is a naturally-occurring amino acid.

In a still further embodiment, the naturally-occurring amino acid is selected from the group consisting of: histidine, phenylalanine, alanine, glutamic acid, aspartic acid, glutamine, leucine, methionine, asparagine, tyrosine, threonine, isoleucine, tryptophan, glycine and valine; yet further, the naturally-occurring amino acid is leucine, isoleucine, alanine or methionine.

In a still further embodiment, the naturally-occurring amino acid is leucine. In another embodiment, the sterically hindered primary amine is a non-naturally occurring amino acid (e.g., 1-aminocyclohexane carboxylic acid, lanthanine or theanine).

In a further embodiment, the sterically hindered primary amine is cyclohexylamine, 2-methylbutylamine or a polymeric amine (e.g., chitosan).

In another embodiment, one or more sterically hindered primary amines may be used in a composition.

In some cases, the sterically hindered primary amine has the formula:

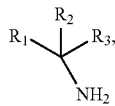

wherein $R_1$, $R_2$ and $R_3$ are independently selected from: H, C(O)OH, C1-C6 alkyl, C1-C6 alkylether, C1-C6 alkylthioether, C1-C6 alkyl carboxylic acid, C1-C6 alkyl carboxylamide and alkylaryl, wherein any group can be singly or multiply substituted with: halogen or amino, and provided that no more than two of $R_1$, $R_2$ and $R_3$ are H.

In another embodiment, no more than one of $R_1$, $R_2$ and $R_3$ is H.

In other embodiments, there is provided a pharmaceutical composition comprising a pharmaceutically acceptable carrier, peptide, a cation selected from $Mg^{2+}$, $Ca^{2+}$, $Zn^{2+}$, $Mn^{2+}$, $K^+$, $Na^+$ or $Al^{3+}$, or a mixture thereof, and a sterically hindered primary amine.

In one embodiment, the cation is $Mg^{2+}$, $Ca^{2+}$ or $Zn^{2+}$ or a mixture thereof.

In a further embodiment, the pharmaceutical composition further comprises a pharmaceutically acceptable binder and/or a pharmaceutically acceptable glidant, lubricant or additive that acts as both a glidant and lubricant and/or an antioxidant.

In some embodiments, the pharmaceutical composition is applied to a carrier.

In some embodiments, the carrier is a filler.

In some cases the molar ratio of cation:sterically hindered primary amine: peptide in the aqueous solution applied to the carrier is 5-100:5-50:1. In some cases, the molar ratio of cation:sterically hindered primary amine may be equal to or greater than 2:1 (e.g., between 5:1 and 2:1). Thus, in some cases the molar ratio of cation:sterically hindered primary amine:peptide applied to the carrier is 100:50:1, 100:30:1, 80:40:1, 80:30:1, 80:20:1, 60:30:1, 60:20:1, 50:30:1, 50:20:1, 40:20:1, 20:20:1, 10:10:1, 10:5:1 or 5:10:1. When binder, e.g., methylcellulose, is present in the GC-C agonist peptide solution applied to the carrier it can be present at 0.5%-2.5% by weight (e.g., 0.7%-1.7% or 0.7%-1% or 1.5% or 0.7%).

In a further embodiment, the pharmaceutical composition further comprises a pharmaceutically acceptable binder or additive, and/or a pharmaceutically acceptable glidant, lubricant or additive that acts as both a glidant and lubricant and/or an antioxidant.

Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well known in the art, as exemplified by Remington's Pharmaceutical Sciences (18th Edition, Mack Publishing Company, 1995).

The compositions described herein may be administered systemically or locally, e.g.: orally (e.g. using capsules, powders, solutions, suspensions, tablets, sublingual tablets and the like), by inhalation (e.g. with an aerosol, gas, inhaler, nebulizer or the like), to the ear (e.g. using ear drops), topically (e.g. using creams, gels, liniments, lotions, ointments, pastes, transdermal patches, etc), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

For treatment of gastrointestinal disorders, the peptides described herein are preferably administered orally, e.g., as a tablet, capsule, sachet containing a predetermined amount of the active ingredient pellet, gel, paste, syrup, bolus, electuary, slurry, powder, lyophilized powder, granules, as a solution or a suspension in an aqueous liquid or a nonaqueous liquid; as an oil-in-water liquid emulsion or a water-in-oil liquid emulsion, via a liposomal formulation (see, e.g., EP 736299) or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein.

The peptides can be co-administered with other agents used to treat gastrointestinal disorders including but not limited to the agents described herein.

In another aspect, suitable pharmaceutical compositions may comprise one or more other therapeutic agents. Such therapeutic agents include, without limitation, analgesic agents; anti-secretory agents, including proton pump inhibitors, acid pump antagonists, H2 receptor antagonists; PDE5 inhibitors; GABA-B antagonists; bile acid sequestrants; prokinetic and promotility agents; antidepressants; antibiotics; antiemetics; and mucosal-protecting agents.

Methods of Treatment

In various embodiments, the peptides and compositions described herein are useful for the treatment of patient gastrointestinal disorder.

In some embodiments, the gastrointestinal disorder is selected from the group consisting of irritable bowel syndrome (IBS), constipation, a functional gastrointestinal disorder, gastroesophageal reflux disease, functional heartburn, dyspepsia, visceral pain, gastroparesis, chronic intestinal pseudo-obstruction, colonic pseudo-obstruction, Crohn's disease, ulcerative colitis, and inflammatory bowel disease.

In a further embodiment, the gastrointestinal disorder is constipation. The constipation can be chronic constipation, idiopathic constipation, due to post-operative ileus, or caused by opiate use. Clinically accepted criteria that define constipation include the frequency of bowel movements, the consistency of feces and the ease of bowel movement. One common definition of constipation is less than three bowel movements per week. Other definitions include abnormally hard stools or defecation that requires excessive straining (Schiller 2001, Aliment Pharmacol Ther 15:749-763). Constipation may be idiopathic (functional constipation or slow transit constipation) or secondary to other causes including neurologic, metabolic or endocrine disorders. These disorders include diabetes mellitus, hypothyroidism, hyperthyroidism, hypocalcaemia, Multiple Sclerosis, Parkinson's disease, spinal cord lesions, Neurofibromatosis, autonomic neuropathy, Chagas disease, Hirschsprung's disease and Cystic fibrosis. Constipation may also be the result of surgery (postoperative ileus) or due to the use of drugs such as analgesics (like opioids), antihypertensives, anticonvulsants, antidepressants, antispasmodics and antipsychotics.

In other embodiments, the gastrointestinal disorder is irritable bowel syndrome (IBS). The irritable bowel syndrome can be constipation-predominant irritable bowel syndrome (c-IBS), diarrhea-predominant irritable bowel syndrome (d-IBS) or alternating between the two irritable bowel syndromes (a-IBS).

In other embodiments, the gastrointestinal disorder is dyspepsia.

In other embodiments, the gastrointestinal disorder is gastroparesis. The gastroparesis can be selected from idiopathic, diabetic or post-surgical gastroparesis.

In still other embodiments, the gastrointestinal disorder is chronic intestinal pseudo obstruction.

In other embodiments, the gastrointestinal disorder is Crohn's disease.

In some embodiments, the gastrointestinal disorder is ulcerative colitis.

In some embodiments, the gastrointestinal disorder is inflammatory bowel disease.

In another embodiment, the gastrointestinal disorder is visceral pain.

In a further embodiment, the present invention features a method for decreasing gastrointestinal pain or visceral pain in a patient, the method comprising, administering to the patient a pharmaceutical composition comprising of peptide described herein. The peptide agonists described herein can be used alone or in combination therapy for the treatment, prevention or reduction of visceral pain associated with a gastrointestinal disorder or pain associated with another disorder.

In another embodiment, the invention features a method for treating inflammation, including inflammation of the gastrointestinal tract, e.g., inflammation associated with a gastrointestinal disorder or infection or some other disorder, the method comprising administering to a patient a pharmaceutical composition comprising a purified peptide described herein.

In another embodiment, the invention features a method for treating a gastrointestinal disorder comprising administering an agonist of the intestinal guanylate cyclase (GC-C) receptor either orally, by rectal suppository, or parenterally.

In still another embodiment, the invention features a method for treating a gastrointestinal disorder comprising administering an agonist of the intestinal guanylate cyclase (GC-C) receptor.

In another embodiment, the invention features a method of increasing guanylate cyclase C (GC-C) receptor activity in a biological sample, tissue (e.g, the intestinal mucosa), or cell (e.g., a cell bearing GC-A receptor), or whole organism.

In another aspect, the invention features a method of increasing the level of cyclic guanosine 3'-monophosphate (cGMP) in a biological sample, tissue (e.g, the intestinal mucosa), or cell (e.g., a cell bearing GC-A receptor), or whole organism by contacting the sample, tissue, or organism to a peptides described herein.

The peptide GC-C receptor agonists described herein can be administered in combination with other agents. For example, the peptides can be administered with an analgesic peptide or compound. The analgesic peptide or compound can be covalently attached to a peptide described herein or it can be a separate agent that is administered together with or sequentially with a peptide described herein in a combination therapy. The peptides described herein may also be administered in combination with other agents used to treat GI disorders including antidepressants, promotility or prokinetic agents, antiemetics, antibiotics, proton pump inhibitors, acid blockers (e.g., histamine H2 receptor antagonists), acid pump antagonists, PDE5 inhibitors, GABA-B agonists, bile acid sequestrants, and mucosal protecting agents.

In some embodiments, useful analgesic agents that may be used with the peptides described herein include Ca channel blockers (e.g., ziconotide), 5HT receptor antagonists (e.g., 5HT3, 5HT4 and 5HT1 receptor antagonists), 5HT4 agonists (e.g., tegaserod [Zelnorm®], mosapride, zacopride, cisapride, renzapride, prucalopride [Resolor®], benzimidazolone derivatives such as BIMU 1 and BIMU 8, and lirexapride), 5HT1 agonists (e.g., sumatriptan and buspirone), opioid receptor agonists (e.g., loperamide, fedotozine, enkephalin pentapeptide, morphine, diphenyloxylate, frakefamide, trimebutine and fentanyl), CCK receptor agonists (e.g., loxiglumide and dexloxiglumide), NK1 receptor antagonists (e.g., aprepitant, vofopitant, ezlopitant, R-673 (Hoffmann-Lä Roche Ltd), SR-48968 and SR-14033, (Sanofi Synthelabo), CP-122,721 (Pfizer, Inc.), GW679769 (Glaxo Smith Kline) and TAK-637 (Takeda/Abbot)), NK2 receptor antagonists (e.g., nepadutant, saredutant, GW597599 (Glaxo Smith Kline), SR-144190 (Sanofi-Synthelabo) and UK-290795 (Pfizer Inc)), NK3 receptor antagonists (e.g., osanetant (SR-142801; Sanofi-Synthelabo), SR-241586 and talnetant), norepinephrine-serotonin reuptake inhibitors (NSRI) (e.g., milnacipran), mixed and selective dopamine receptor antagonists (e.g.—metoclopramide, itopride, domperidone), vanilloid and cannabanoid receptor agonists, sialorphin and sialorphin-related peptides. Analgesics agents in the various classes are described in the literature.

In some embodiments, one or more other therapeutic agents may be used in combination with the peptides described herein. Such agents include antidepressants, promotility or prokinetic agents, antiemetics, antibiotics, proton pump inhibitors, acid blockers (e.g., histamine H2 receptor antagonists), acid pump antagonists, PDE5 inhibitors, GABA-B agonists, bile acid sequestrants, and mucosal protecting agents.

Examples of antidepressants include, without limitation, tricyclic antidepressants such as amitriptyline (Elavil®), desipramine (Norpramin®), imipramine (Tofranil®), amoxapine (Asendin®), nortriptyline; the selective serotonin reuptake inhibitors (SSRI's) such as paroxetine (Paxil®), fluoxetine (Prozac®), sertraline (Zoloft®), and citralopram (Celexa®); and others such as doxepin (Sinequan®) and trazodone (Desyrel®).

Examples of promotility and prokinetic agents include, without limitation, itopride, octreotide, bethanechol, metoclopramide (Reglan®), domperidone (Motilium®), erythromycin (and derivatives thereof) and cisapride (Propulsid®). An example of antiemetics includes, without limitation, prochlorperazine.

Examples of antibiotics that may be used include those that may be used to treat *Heliobacter pylori* infections, such as amoxicillin, tetracycline, metronidazole, or clarithromycin. Other antibiotics such as erythromycin and derivatives thereof may also be used in combination with the peptides described herein.

Examples of proton pump inhibitors include, without limitation, omeprazole (Prilosec®), esomeprazole (Nexium®), lansoprazole (Prevacid®), pantoprazole (Protonix®) and rabeprazole (Aciphex®). Examples of H2 receptor blockers include, without limitation, including cimetidine, ranitidine, famotidine and nizatidine. Examples of acid pump antagonists include, without limitation, revaprazan, CS-526 (J. Pharmacol. Exp. Ther. (2007) 323: 308-317), PF-03716556 (J. Pharmacol. Exp. Ther. (2009) 328(2):671-9), and YH1885 (Drug Metab. Dispos. (2001) 29(1):54-9).

Examples of PDE5 inhibitors include, without limitation, avanafil, lodenafil, mirodenafil, sildenafil citrate, tadalafil, vardenafil and udenafil. GABA-B agonists include, without limitation, baclofen and XP19986 (CAS Registry No. 847353-30-4). Examples of bile acid sequestrants include, without limitation, GT102-279, cholestyramine, colesevelam, colesevelam hydrochloride, ursodeoxycholic acid, colestipol, colestilan, sevelamer, polydiallylamine crosslinked with epichlorohydrin, dialkylaminoalkyl derivatives of a cross-linked dextran, and N-(cycloalkyl)alkylamines. Examples of mucosal protecting agents include, without limitation, sucralfate (Carafate), teprenone, polaprezinc, cetraxate and bismuth subsalicyclate.

Combination therapy can be achieved by administering two or more agents, e.g., a peptide described herein and another therapeutic peptide or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

Dosage

The dose range for adult humans may be generally from 5 µg to 100 mg/day orally of the peptides described herein. Tablets, capsules, or other forms of presentation provided in discrete units may conveniently contain an amount of compound described herein which is effective at such dosage or as a multiple of the same, for instance, units containing 25 µg to 2 mg or around 100 µg to 1 mg. The precise amount of compound prescribed to a patient will be the responsibility of the attendant physician. However, the dose employed will depend on a number of factors, including the age and sex of the patient, the precise disorder being treated, and its severity.

In other embodiments, the dose is 50 µg, 67.5 µg, 100 µg, 133 µg, 145 µg, 150 µg, 200 µg, 266 µg, 290 µg, 300 µg, 400 µg, 500 µg or 600 µg per day orally.

In various embodiments, the dosage unit is administered with food at any time of the day, without food at any time of the day, with food after an overnight fast (e.g. with breakfast), at bedtime after a low fat snack.

In one particular embodiment, the dosage unit is administered prior to or subsequent to food consumption (e.g., a meal).

In a further embodiment, the dosage unit is administered approximately 15 minutes to 1 hour prior to food consumption.

In various embodiments, the dosage unit is administered once a day, twice a day, three times a day, four times a day, five times a day or six times a day. In certain embodiments the dosage unit and daily dose are equivalent.

The precise amount of each of the two or more active ingredients in a dosage unit will depend on the desired dosage of each component. Thus, it can be useful to create a dosage unit that will, when administered according to a particular dosage schedule (e.g., a dosage schedule specifying a certain number of units and a particular timing for administration), deliver the same dosage of each component as would be administered if the patient was being treated with only a single component.

In other circumstances, it might be desirable to create a dosage unit that will deliver a dosage of one or more components that is less than that which would be administered if the patient was being treated only with a single component.

Finally, it might be desirable to create a dosage unit that will deliver a dosage of one or more components that is greater than that which would be administered if the patient was being treated only with a single component.

The pharmaceutical composition can include additional ingredients including but not limited to the excipients described herein. In certain embodiments, one or more therapeutic agents of the dosage unit may exist in an extended or control release formulation and additional therapeutic agents may not exist in extended release formulation. For example, a peptide or agonist described herein may exist in a controlled release formulation or extended release formulation in the same dosage unit with another agent that may or may not be in either a controlled release or extended release formulation. Thus, in certain embodiments, it may be desirable to provide for the immediate release of one or more of the agents described herein, and the controlled release of one or more other agents.

The present invention has been described with reference to certain exemplary embodiments thereof. However, it will be readily apparent to those skilled in the art that it is possible to embody the invention in specific forms other than those of the exemplary embodiments described above. This may be done without departing from the spirit of the invention. The exemplary embodiments are merely illustrative and should not be considered restrictive in any way. The scope of the invention is defined by the appended claims and their equivalents, rather than by the preceding description.

EXAMPLES

The GC-C agonist peptides or pharmaceutically acceptable salts thereof as described herein were prepared by solid phase chemical synthesis and natural folding (air oxidation) by American Peptide Company (Sunnyvale, Calif.). In some cases, the peptides were modified after synthesis as described herein. The $Cys^1$-α-Ketone peptide was synthesized, for example, by adding 1.5 L methanol/dimethylformamide (9:1 v/v) and 28.8 g 3,5-di-tert-butyl-1,2-benzoquinone (10 equivalents) to 20 g (13.1 mmol) of linaclotide and was stirred for 1 hour at room temperature. Schiff base formation was monitored by HPLC. Once all the linaclotide was consumed, 17 L of 0.1 M HCl were added in and the reaction mixture was stirred for 2 days. The reaction mixture was filtered, extracted twice with dichloromethane, and the resulting aqueous solution was applied to a preparative scale reverse-phase HPLC C-18 column to purify the $Cys^1$-α-Ketone. The HPLC column used in preparative HPLC was a 2-inch-diameter, $C_{18}$ column equilibrated with mobile phase A (0.05% acetic acid in water). Unbound material was washed with mobile phase A at a flow rate of 100 mL/min, and peptide-related material was eluted with a linear gradient of mobile phase B (acetonitrile) from 10% to 40% over 60 minutes. Fractions containing Cys1-Ketone were pooled followed by solvent removal through lyophilization.

Example 1: cGMP Accumulation in T84 Cells for Analysis of GC-C Activity

T84 cells, a human colon carcinoma cell line, were obtained from ATCC (P/N CCL-248) and cultured in T-150 flasks to 60-70% confluency. The monolayers were lifted with trypsin and used to seed 96-well tissue culture plates (Costar, P/N 3596) at a cell density of $2.0 \times 10^5$ cells/well, which were grown overnight in a 5% carbon dioxide environment with 2 mM Dulbecco's modified Eagle's medium (DMEM)/F-12 50/50 nutrient mixture supplemented with 5% fetal bovine serum (FBS) and L-glutamine (Mediatech, P/Ns 10-092-CV, 35-0150CV, and 25-005-C1, respectively).

After overnight incubation, 96-well plates seeded with $2.0 \times 10^5$ cells/well were washed twice with 0.2 mL of DMEM (Mediatech, P/N 10-013-CV) without added supplements. To inhibit any phophodiesterase activity, the cells were incubated with 0.180 mL of 1 mM 3-isobutyl-1-methylxanthine (IBMX; Sigma P/N 15879) in DMEM for 10 min at 37° C. Standard curves ranging from 0.1 to 10,000 nM (final concentration) were prepared for each test article using a Hamilton Microlab Robot (Model STARlet). The GC-C activity assay was conducted by incubating 0.02 mL of each standard with 0.180 mL of 1 mM IBMX in DMEM in a 96-well plate for 30 minutes at 37° C. After the incubation, the supernatants were removed and the cells were lysed with cold 0.1 M hydrochloric acid (HCl) for 30 min on ice. A volume of 175 µL/well of each lysate was transferred to new 96-well plates (Waters, P/N 186002481) and centrifuged at 1,000×g for 10 min to remove any cell debris. The resulting supernatants were transferred in 90 aliquots to new 96-well plates and neutralized to pH 7 with 90 µL of 1 M ammonium acetate. The centrifuged and neutralized T84 cell lysates were analyzed using liquid chromatography with tandem mass spectrometry detection (LC/MS/MS). The method outlined in Table 1 was used to quantify the concentration of guanosine 3',5'-cyclic monophosphate (cGMP) in each cell lysate sample. Cyclic GMP purchased from Sigma (P/N G6129) was used to prepare a standard curve in 0.1 M HCl. Each standard was neutralized with an equal volume of ammonium acetate, resulting in a cGMP standard curve ranging from 1 to 1,024 nM (final concentration).

The cyclic GMP concentrations were determined from each sample using the LC/MS conditions (Table 1 below) and calculated standard curve. Analyte peak areas were used to generate a 1/x2-weighted linear calibration curve, which was used to extrapolate the cGMP concentration in each sample. The half maximal effective concentration ($EC_{50}$) value for each test article was generated using GraphPad Prism Version 5.01 (GraphPad Software, San Diego, Calif.). To determine the differences in EC50 values were statistically significant, the average activity curve of each drug product degradant was compared to a linaclotide control using the F-test in the GraphPad software. For these comparisons, a p-value was determined, with a value≤0.05 indicating a significant difference in GC-C agonist activity.

TABLE 1

LC/MS Parameters for the Quantitation of cGMP in T84 Cells

| MS: | Thermo Quantum |
| --- | --- |
| Ion Mode: | Electrospray, positive mode ($ESI^+$) |
| Scan Type: | Mulitple reaction monitoring (MRM) |

| Compound: cGMP | Transition | Dwell Time (msec) | Collision Energy (V) | Tube Lens | Retention Time (min) | LLOQ (nM) |
| --- | --- | --- | --- | --- | --- | --- |
| | 346 > 152 | 100 | 28 | 139 | 0.8 | 1 |

| HPLC: | Waters Acquity UPLC |
| --- | --- |
| Column: | Hypersil Gold C18, 2.1 × 50 mm, 1.9 um |
| Guard Column: | Hypersil Gold, 2.1 × 10 mm, 1.9 um |
| Flow Rate: | 400 µL/min |
| Column Temp: | RoomTemperature |
| Autosampler Temp: | 6° C. |
| Injection Volume: | 20 µL |
| Mobile Phases: | A = 0.1% formic acid in 98/2 water/acetonitrile<br>B = 0.1% formic acid in 2/98 water/acetonitrile |

| | Time (min) | % A | % B |
| --- | --- | --- | --- |
| Gradient: | 0 | 100 | 0 |
| | 0.5 | 60 | 40 |
| | 1.1 | 60 | 40 |
| | 1.75 | 5 | 95 |
| | 2.5 | 5 | 9 |
| | 2.6 | 100 | 0 |

Example 2: Relative Binding Affinity of Exemplary Peptides to the GC-C Receptor of T84 Cells The relative binding affinities of linaclotide and $Cys^1$-α-Ketone to the guanylate cyclase-C receptor (GC-C) were determined using a competitive-binding assay in which the peptides competed with a known GC-C agonist, porcine-derived heat-stable enterotoxin (pSTa), for binding sites on cell-surface GC-C receptors on human colonic epithelial (T84) cells. The pSTa, i.e. MM 416251, was radiolabeled with $^{125}$I to enable measurement of its receptor binding. The competitive-binding assay was performed by adding various concentrations of each peptide (0.1 to 3,000 nM) to 0.20 mL reaction mixtures containing Dulbecco's modified Eagle's medium (DMEM), 0.5% bovine serum albumin (BSA), $2.0 \times 10^5$ T84 cells, and 170 pM [$^{125}$I]-pSTa (200,000 cpm). After incubation at 37° C. for 60 min, the reaction mixtures were applied to glass-fiber filters by vacuum filtration to isolate receptor-bound material. The concentration of bound radioligand trapped on the filter was then measured by scintillation counting. For each peptide, the reaction with the lowest amount of competitor was used to determine the maximal specific binding of the radioligand. The non-specific binding of [$^{125}$I]-pSTa was measured in the reactions containing 3,000 nm of each test peptide. The data were used to construct competitive radioligand-binding curves and determine the relative binding affinities of linaclotide and Cys$^1$-α-Ketone, as measured by their IC$_{50}$ and K$_i$ values.

Both linaclotide and Cys$^1$-α-Ketone competitively inhibited the specific binding of [$^{125}$I]-pSTa to cell-surface GC-C receptors on T84 cells. Their relative binding affinities, as measured by their inhibition constants (K$_i$), were as follows: Linaclotide K$_i$=3.9±1.6 nM and Cys$^1$-α-Ketone K$_i$=5.2±0.9 nM (FIG. 1).

Example 3: cGMP Response in T84 Cells Induced by Exemplary Peptides

Linaclotide and Cys$^1$-α-Ketone were tested for guanylate cyclase-C (GC-C) agonist activity in T84 cells as follows. In each well of a 96-well plate, approximately 200,000 T84 cells/well was first incubated with 1 mM 3-isobutyl-1-methylxanthine (IBMX) in 0.18 mL of Dulbecco's modified Eagle's medium (DMEM) for 10 minutes at 37° C. Each peptide was diluted to final concentrations ranging from 0.1 to 10,000 nM, and 0.02 mL of each dilution was added in duplicate to a 96-well plate containing the T84 cells, for a final volume of 0.2 mL per well. The peptide reactions were incubated for 30 min at 37° C. Following the incubation, the supernatants were removed and discarded and the cells were lysed with cold 0.1 M hydrochloric acid (HCl) for 30 min on ice. The cell debris was removed by centrifugation and the concentration of guanosine 3',5'-cyclic monophosphate (cyclic GMP) in each lysate was determined using liquid chromatography with tandem mass spectrometry. The data were used to construct dose-response curves and calculate half-maximal effective concentration (EC$_{50}$) values for each test article.

Figure 2:
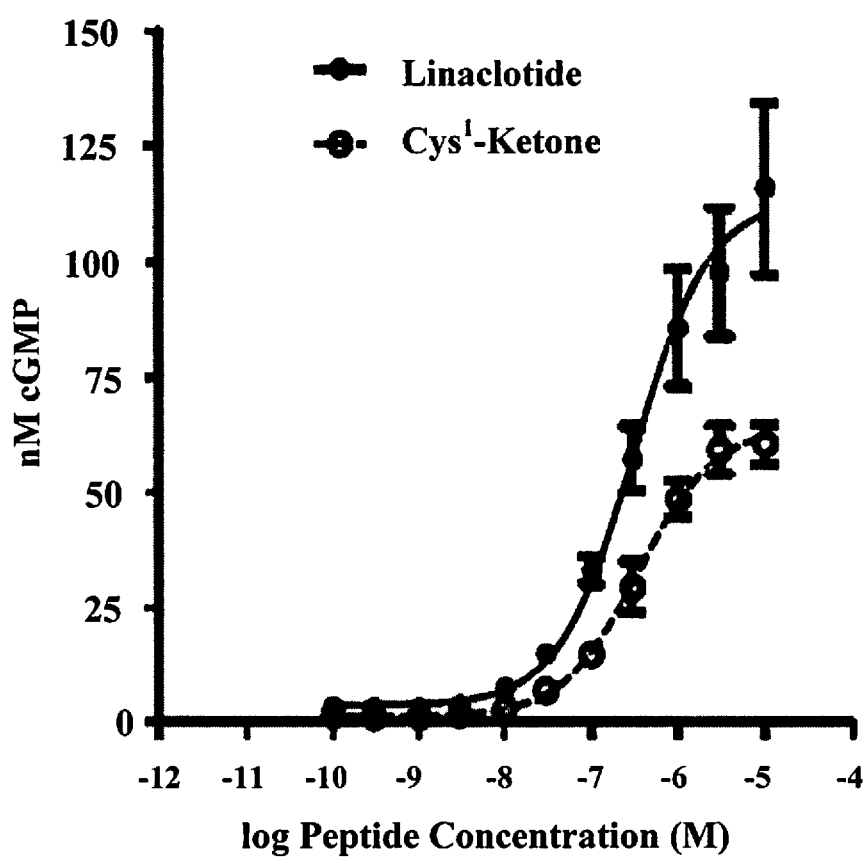
FIG. 2 shows the dose response of exemplary peptides of the present invention in a T84 cell cGMP assay.

Linaclotide and Cys$^1$-α-Ketone showed GC-C agonist activity in T84 cells, as measured by the increase in intracellular cGMP (FIG. 2). The EC$_{50}$ values for linaclotide and Cys$^1$-α-Ketone were 315±105-nM and 352±55 nM, respectively. Comparison of the dose-response curve of linaclotide to that of Cys$^1$-α-Ketone using the F-test indicated that the EC$_{50}$ values are not statistically different (p=0.8884).

Example 4: Measurement of Content and Purity of Exemplary Peptides

Cys$^1$-α-Ketone Peptide

Linaclotide drug product (as described in US 2010/0048489, incorporated by reference herein) was stressed by incubating 20 g of drug product beads containing 1 mg of linaclotide sprayed onto 224-mg Avicel beads for two months at 40° C. with 75% RH. The peptide-related material was extracted from the beads with 20 mL of 0.1 N HCl and gentle agitation in a vortex mixer for one hour at room temperature. The resulting suspension was centrifuged at 1,000×g for five minutes to pellet the beads and the supernatent containing extracted peptides was lyophilized. The dried sample was reconstituted in 2.5 mL of 0.1 N HCl and Cys-α-Ketone was isolated and purified by preparative HPLC using method as follows A YMC Pro™ C18 column (dimensions: 3.0×150 mm, 3.5 um, 120 Å; Waters Corp., Milford, Mass.) or equivalent is used and is maintained at 40° C. Mobile phase A (MPA) consists of 98:2 water/acetonitrile containing 0.1% trifluoroacetic acid while mobile phase B (MPB) consists of 5:95 water/acetonitrile containing 0.1% trifluoroacetic acid. Elution of the peptides is accomplished with a gradient from 82% to 78% MPA and 18% to 22% MPB in 12 minutes followed by a ramp to 50% MPA and 50% MPB in 1 minute with a 3 minute hold at 50% MPA and 50% MPB followed by a wash of 82% MPA and 18% MPB for 7 minutes. The flow rate is 0.6 mL/min and detection is accomplished by UV at 220 nm.

Fractions were collected manually and those containing Cys$^1$-α-Ketone were pooled and lyophilized to dryness. The dried residue was reconstituted in 1.6 mL of water to give a final concentration of 0.5 mg/mL and was stored frozen at −20° C. An aliquot of purified Cys$^1$-α-Ketone was tested by analytical HPLC with the method described below and purity was determined to be 90.7%.

Content and purity of the peptides of the present invention may be determined by reverse phase gradient liquid chromatography using an Agilent Series 1100 LC System with Chemstation Rev A.09.03 software or equivalent. A YMC Pro™ C18 column (dimensions: 3.0×150 mm, 3.5 um, 120 Å; Waters Corp., Milford, Mass.) or equivalent is used and is maintained at 40° C. Mobile phase A (MPA) consists of water with 0.1% trifluoroacetic acid while mobile phase B (MPB) consists of 95% acetonitrile:5% water with 0.1% trifluoroacetic acid. Elution of the peptides is accomplished with a gradient from 0% MPB for 4 minutes followed by 10% MPB for 5 minutes followed by 23% MPB for 34 minutes followed by 34% MPB for 6 minutes followed by 80% MPB for 10 minutes. Re-equilibration of the column is performed by returning to 0% MPB in 1 minute followed by a 7 minute hold at 100% MPA. The flow rate is 0.6 mL/min and detection is accomplished by UV at 220 nm.

Figure 3:
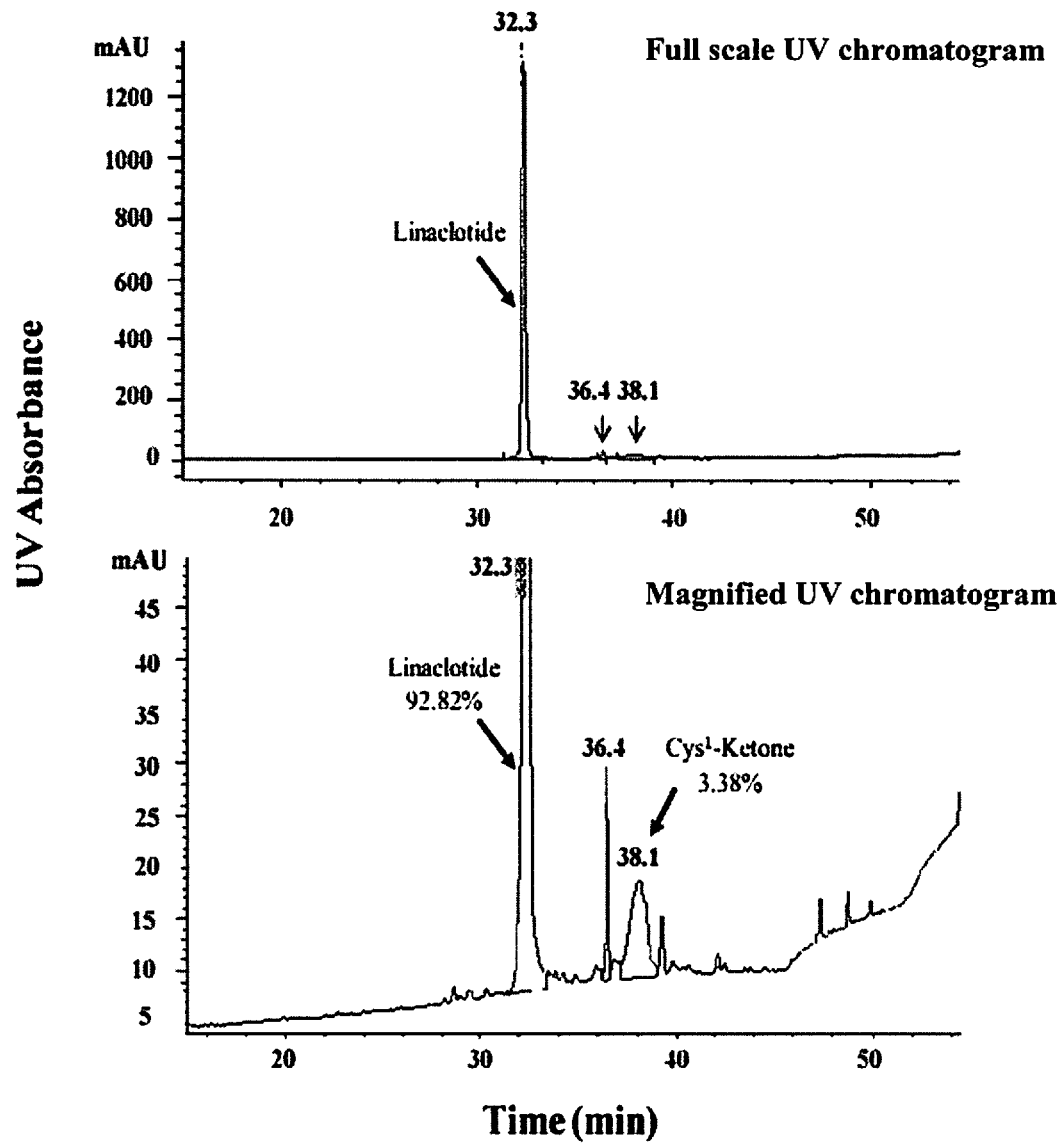
FIG. 3 demonstrates an example of an analysis of exemplary peptides by RP-HPLC, wherein "Cys$^1$-α-Ketone" refers to the linaclotide ketone derivative modified on its N-terminal α-amine group.

An example of an analysis of linaclotide and Cys$^1$-α-Ketone product by RP-HPLC is shown in FIG. 3.

The contents of the purified peptides were measured by determining the peptide concentration in the prepared sample against a similarly prepared external peptide standard.

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

```
                         SEQUENCE LISTING

<160> NUMBER OF SEQ ID NOS: 9

<210> SEQ ID NO 1
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 1

Cys Cys Glu Tyr Cys Cys Asn Pro Ala Cys Thr Gly Cys Tyr
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Xaa1 is a Cys, wherein the alpha-amine of the
      Cys is deaminated.
<220> FEATURE:
<221> NAME/KEY: DISULFID
<222> LOCATION: (1)..(6)
<223> OTHER INFORMATION: Disulfide bond is between the deaminated
      alpha-amine of Xaa1 and Cys6.
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 2

Xaa Cys Glu Tyr Cys Cys Asn Pro Ala Cys Thr Gly Cys Tyr
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(6)
<223> OTHER INFORMATION: Trisulfide bond between Cys1 and Cys6.
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 3
```

```
Cys Cys Glu Tyr Cys Cys Asn Pro Ala Cys Thr Gly Cys Tyr
1               5                   10
```

<210> SEQ ID NO 4
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: MISC_FEATURE
<222> LOCATION: (5)..(13)
<223> OTHER INFORMATION: Trisulfide bond between Cys5 and Cys13.

<400> SEQUENCE: 4

```
Cys Cys Glu Tyr Cys Cys Asn Pro Ala Cys Thr Gly Cys Tyr
1               5                   10
```

<210> SEQ ID NO 5
<211> LENGTH: 14
<212> TYPE: PRT
<213> ORGANISM: Artificial Sequence
<220> FEATURE:
<223> OTHER INFORMATION: Synthetically generated sequence
<220> FEATURE:
<221> NAME/KEY: DISULFID
<222> LOCATION: (1)..(6)
<220> FEATURE:
<221> NAME/KEY: MISC_FEATURE
<222> LOCATION: (2)..(10)
<223> OTHER INFORMATION: Trisulfide bond between Cys2 and Cys10.
<220> FEATURE:
<221> NAME/KEY: DISULFID
<222> LOCATION: (5)..(13)

<400> SEQUENCE: 5

```
Cys Cys Glu Tyr Cys Cys Asn Pro Ala Cys Thr Gly Cys Tyr
1               5                   10
```

<210> SEQ ID NO 6
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Xaa1 is a Cys, wherein the alpha-amine of the
      Cys which is cross-linked to the amine group of Cys2 to form an
      imidazolidinone 5 membered ring at the N-terminus of the peptide.
<220> FEATURE:
<221> NAME/KEY: DISULFID
<222> LOCATION: (1)..(6)
<223> OTHER INFORMATION: Disulfide bond is between the imidazolidinone
      5-membered ring of Xaa1 and Cys6.
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 6

```
Xaa Cys Glu Tyr Cys Cys Asn Pro Ala Cys Thr Gly Cys Tyr
1               5                   10
```

```
<210> SEQ ID NO 7
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (2)..(13)

<400> SEQUENCE: 7

Cys Cys Glu Tyr Cys Cys Asp Pro Ala Cys Thr Gly Cys Tyr
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 8

Cys Cys Glu Tyr Cys Cys Asn Pro Ala Cys Thr Gly Cys Tyr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 9

Cys Cys Glu Tyr Cys Cys Asn Pro Ala Cys Thr Gly Cys
1               5                   10
```

What is claimed is:

1. A peptide or a pharmaceutically acceptable salt thereof, wherein the peptide comprises the amino acid structure of:

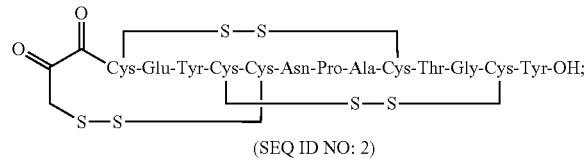

(SEQ ID NO: 2)

and the peptide activates the guanylate cyclase C receptor.

2. The peptide or a pharmaceutically acceptable salt thereof according to claim 1, wherein the peptide consists of the amino acid structure of:

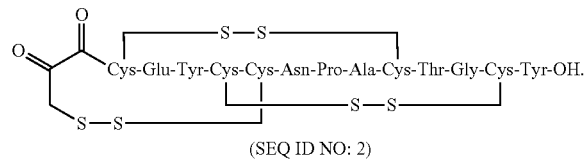

(SEQ ID NO: 2)

3. The peptide or pharmaceutically acceptable salt thereof according to claim 2, wherein said peptide or pharmaceutically acceptable salt thereof is isolated or purified.

4. A pharmaceutical composition comprising the peptide or pharmaceutically acceptable salt thereof according to claim 2.

5. The pharmaceutical composition of claim 4 further comprising linaclotide, wherein the peptide or pharmaceutically acceptable salt thereof comprises between 0.01-5% by weight compared to the weight of linaclotide in the pharmaceutical composition.

6. The pharmaceutical composition of claim 4, further comprising linaclotide and one or more peptides selected from:

i. the peptide consisting of the amino acid structure of:

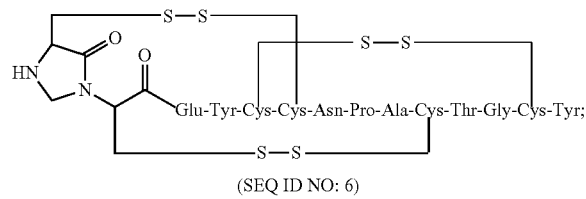

(SEQ ID NO: 6)

ii. the peptide consisting of the amino acid structure of:

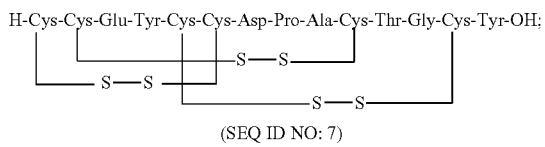

(SEQ ID NO: 7)

iii. the peptide consisting of the amino acid structure of:

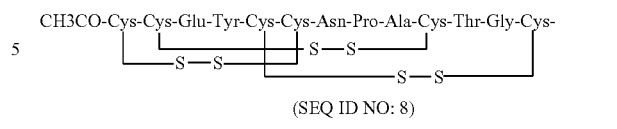

(SEQ ID NO: 8)

iv. the peptide consisting of the amino acid structure of:

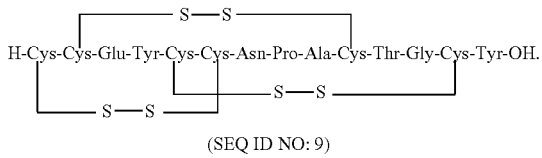

(SEQ ID NO: 9)

7. The pharmaceutical composition of claim 4, further comprising
i. linaclotide; or
ii. the peptide or a pharmaceutically acceptable salt thereof consisting of the amino acid structure of:

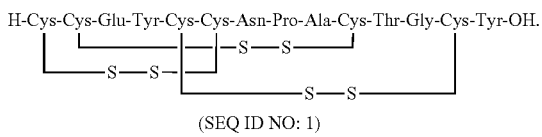

(SEQ ID NO: 1)

8. The pharmaceutical composition according to claim 7 further comprising one or more agents selected from (i) a cation selected from $Mg^{2+}$, $Ca^{2+}$, $Zn^{2+}$, $Mn^{2+}$, $K^+$, $Na^+$ or $Al^{3+}$, or (ii) a naturally-occurring amino acid.

9. The pharmaceutical composition according to claim 8, wherein said $Mg^{2+}$, $Ca^{2+}$, $Zn^{2+}$, $Mn^{2+}$, $K^+$, $Na^+$ or $Al^{3+}$ is provided as magnesium acetate, magnesium chloride, magnesium phosphate, magnesium sulfate, calcium acetate, calcium chloride, calcium phosphate, calcium sulfate, zinc acetate, zinc chloride, zinc phosphate, zinc sulfate, manganese acetate, manganese chloride, manganese phosphate, manganese sulfate, potassium acetate, potassium chloride, potassium phosphate, potassium sulfate, sodium acetate, sodium chloride, sodium phosphate, sodium sulfate, aluminum acetate, aluminum chloride, aluminum phosphate or aluminum sulfate.

10. The pharmaceutical composition according to claim 8, wherein the naturally-occurring amino acid is histidine, phenylalanine, alanine, glutamic acid, aspartic acid, glutamine, leucine, methionine, asparagine, tyrosine, threonine, isoleucine, tryptophan or valine.

11. The pharmaceutical composition according to claim 10, wherein said pharmaceutical composition further comprises $Mg^{2+}$, $Ca^{2+}$, $Zn^{2+}$, $Mn^{2+}$, $K^+$, $Na^+$ or $Al^{3+}$.

12. The pharmaceutical composition according to claim 11, wherein said $Mg^{2+}$, $Ca^{2+}$, $Zn^{2+}$, $Mn^{2+}$, $K^+$, $Na^+$ or $Al^{3+}$ is provided as magnesium acetate, magnesium chloride, magnesium phosphate, magnesium sulfate, calcium acetate, calcium chloride, calcium phosphate, calcium sulfate, zinc acetate, zinc chloride, zinc phosphate, zinc sulfate, manganese acetate, manganese chloride, manganese phosphate, manganese sulfate, potassium acetate, potassium chloride, potassium phosphate, potassium sulfate, sodium acetate, sodium chloride, sodium phosphate, sodium sulfate, aluminum acetate, aluminum chloride, aluminum phosphate or aluminum sulfate.

13. The pharmaceutical composition according to claim 8 further comprising an antioxidant, a pharmaceutically acceptable binder or additive, a pharmaceutically acceptable filler, or an additional therapeutic agent.

14. The pharmaceutical composition according to claim 13, wherein said antioxidant is BHA, vitamin E or propyl gallate.

15. The pharmaceutical composition according to claim 13, wherein the pharmaceutically acceptable binder or additive is selected from polyvinyl alcohol, polyvinyl pyrrolidone (povidone), a starch, maltodextrin or a cellulose ether.

16. The pharmaceutical composition of claim 15, wherein the cellulose ether is selected from: methylcellulose, ethylcellulose, carboxymethylcellulose, hydroxyethyl cellulose, hydroxyethyl methylcellulose, hydroxypropyl cellulose and hydroxypropyl methylcellulose.

17. The pharmaceutical composition according to claim 13, wherein the pharmaceutically acceptable filler is cellulose, isomalt, mannitol or dibasic calcium phosphate.

18. The pharmaceutical composition of claim 17, wherein the cellulose is selected from microfine cellulose and microcrystalline cellulose.

19. A dosage unit comprising a pharmaceutical composition according to claim 7.

20. The dosage unit according to claim 19, wherein said dosage unit is a capsule or tablet.

21. The dosage unit according to claim 19, wherein each of said dosage units comprises 5 µg to 1 mg of linaclotide.

22. The dosage unit according to claim 19, wherein each of said dosage units comprises 290 µg or 145 µg of linaclotide.

23. A method for increasing intestinal motility in a patient, the method comprising administering to the patient an effective amount of the pharmaceutical composition according to claim 7.

24. A method for treating a gastrointestinal disorder comprising administering the pharmaceutical composition according to claim 7 or 5.

25. The method of claim 24, wherein the gastrointestinal disorder is selected from the group consisting of: irritable bowel syndrome (IBS), constipation, a functional gastrointestinal disorder, gastroesophageal reflux disease, functional heartburn, dyspepsia, visceral pain, gastroparesis, chronic intestinal pseudo-obstruction, colonic pseudo-obstruction, Crohn's disease, ulcerative colitis, and inflammatory bowel disease.

26. The method of claim 25, wherein the constipation is chronic constipation, idiopathic constipation, due to post-operative ileus, or caused by opiate use.

27. The method of claim 25, wherein the irritable bowel syndrome is constipation-predominant irritable bowel syndrome (c-IBS), diarrhea-predominant irritable bowel syndrome (d-IBS) or alternating between the two irritable bowel syndromes (a-IBS).

28. The method according to claim 25, wherein said gastroparesis is idiopathic, diabetic or post-surgical gastroparesis.

* * * * *

UNITED STATES PATENT AND TRADEMARK OFFICE
CERTIFICATE OF CORRECTION

PATENT NO.        : 9,708,371 B2
APPLICATION NO.   : 14/239178
DATED             : July 18, 2017
INVENTOR(S)       : Marco Kessler et al.

It is certified that error appears in the above-identified patent and that said Letters Patent is hereby corrected as shown below:

In the Claims

Column 38, Line 15, cancel the "Tyr–" before the terminal –OH.

Column 38, Line 25, replace the text "ii. the peptide" with "ii. a pepetide".

Signed and Sealed this
Tenth Day of April, 2018

Andrei Iancu
*Director of the United States Patent and Trademark Office*